United States Patent
Py

(10) Patent No.: US 8,318,091 B2
(45) Date of Patent: Nov. 27, 2012

(54) TRANSFER PORT AND METHOD FOR TRANSFERRING STERILE ITEMS

(76) Inventor: Daniel Py, Stamford, CT (US)

(*) Notice: Subject to any disclaimer, the term of this patent is extended or adjusted under 35 U.S.C. 154(b) by 0 days.

(21) Appl. No.: 13/454,910

(22) Filed: Apr. 24, 2012

(65) Prior Publication Data
US 2012/0227359 A1    Sep. 13, 2012

Related U.S. Application Data

(62) Division of application No. 10/241,249, filed on Sep. 10, 2002, now Pat. No. 8,163,251.

(60) Provisional application No. 60/318,546, filed on Sep. 10, 2001.

(51) Int. Cl.
| | |
|---|---|
| B01J 19/00 | (2006.01) |
| A61L 2/04 | (2006.01) |
| B65G 25/00 | (2006.01) |
| B66C 17/08 | (2006.01) |
| B65B 11/52 | (2006.01) |
| B65B 53/00 | (2006.01) |

(52) U.S. Cl. ............ 422/40; 422/307; 414/147; 53/427; 53/441; 53/509

(58) Field of Classification Search .................. None
See application file for complete search history.

(56) References Cited

U.S. PATENT DOCUMENTS

| | | |
|---|---|---|
| 4,335,075 A | 6/1982 | Kackos |
| 4,557,825 A | 12/1985 | Wittes et al. |
| 5,074,951 A | 12/1991 | Banco et al. |
| 5,446,289 A | 8/1995 | Shodeen et al. |
| 5,447,699 A | 9/1995 | Papciak et al. |
| 5,460,439 A | 10/1995 | Jennrich et al. |
| 5,525,295 A | 6/1996 | Pflug et al. |
| 5,571,476 A | 11/1996 | Newman |
| 5,638,988 A | 6/1997 | Rogers et al. |
| 5,649,801 A | 7/1997 | White |
| 5,715,659 A | 2/1998 | Norton |
| 5,743,313 A | 4/1998 | Josefsson |
| 5,799,464 A | 9/1998 | Olsson |
| 5,816,772 A | 10/1998 | Py |
| 6,048,493 A | 4/2000 | Melgaard et al. |
| 6,062,808 A | 5/2000 | Masujima et al. |
| 6,207,119 B1 | 3/2001 | Diccianni et al. |
| 6,488,972 B1 | 12/2002 | Cerani |
| 6,718,736 B2 | 4/2004 | Oguri et al. |

FOREIGN PATENT DOCUMENTS

| | | |
|---|---|---|
| EP | 0537117 A1 | 4/1993 |
| FR | 1506930 | 11/1967 |
| GB | 860028 | 2/1961 |
| GB | 1146767 | 3/1969 |
| WO | WO9801363 * | 1/1998 |

* cited by examiner

*Primary Examiner* — Walter D Griffin
*Assistant Examiner* — Christopher Vandeusen
(74) *Attorney, Agent, or Firm* — McCarter & English, LLP

(57) ABSTRACT

A sterile enclosure contains a transfer module defining a window. A port covers the window to maintain the inside of the enclosure as a sealed and sterile environment. A sliding, heated cutting element mounted on the port serves to sterilize and sever a portion of a sterile transfer bag assembly attached to the port. Preferably, the excised portion of the sterile transfer bag assembly is affixed to the port when the port opens. The sliding cutting element remains extended and heated to prevent contamination when the port is open. Further, a heating element is mounted about the window in order to sterilize around the opening when the port is open.

16 Claims, 27 Drawing Sheets

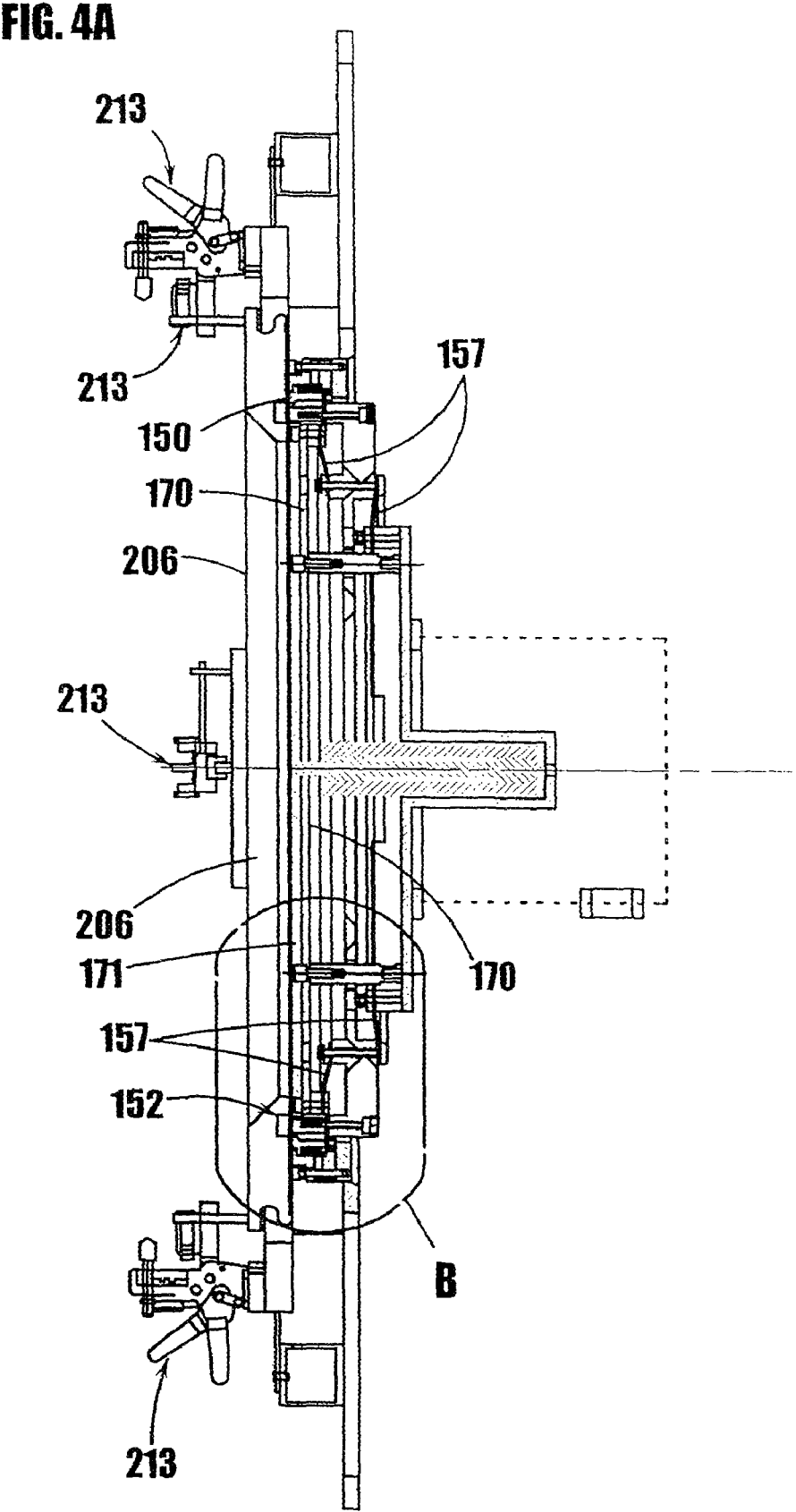

FIG. 6B
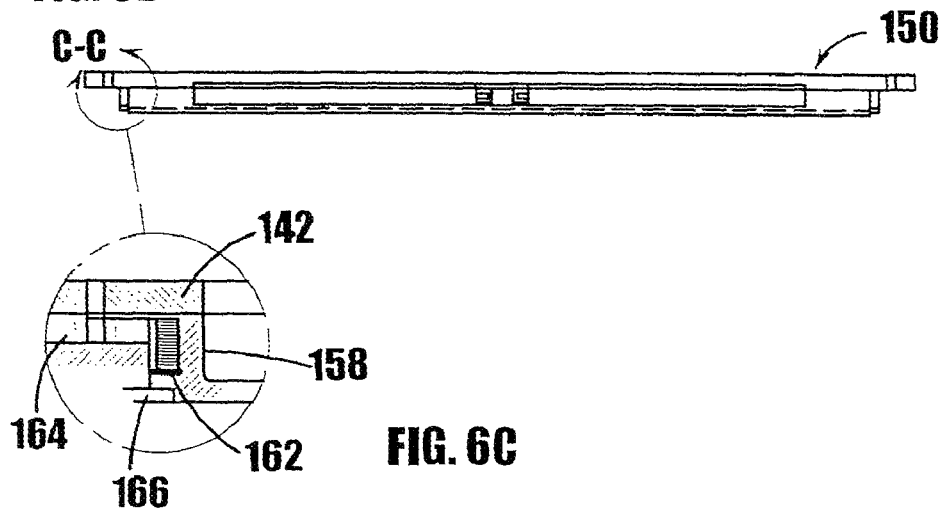
FIG. 6C
FIG. 6A
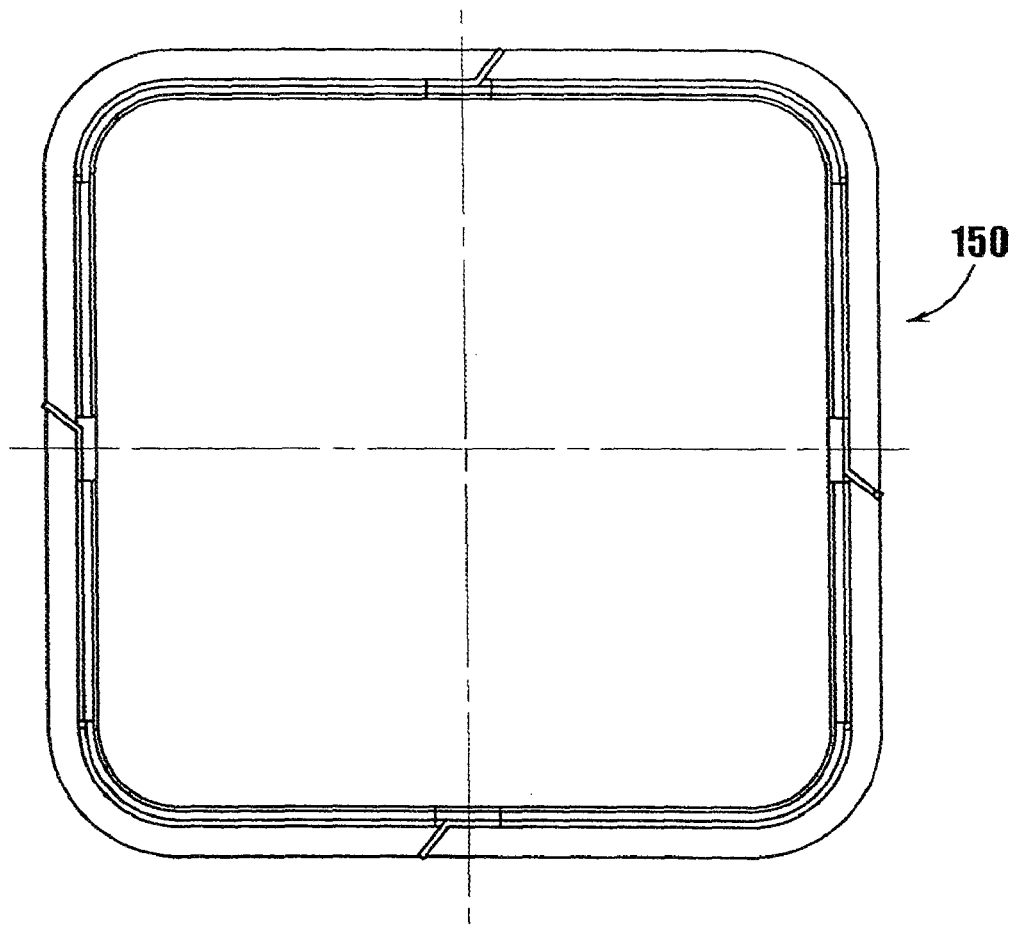

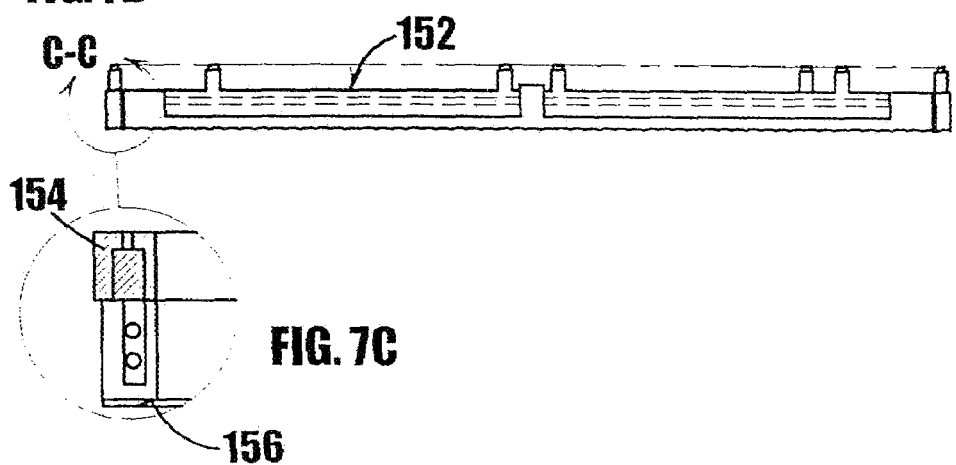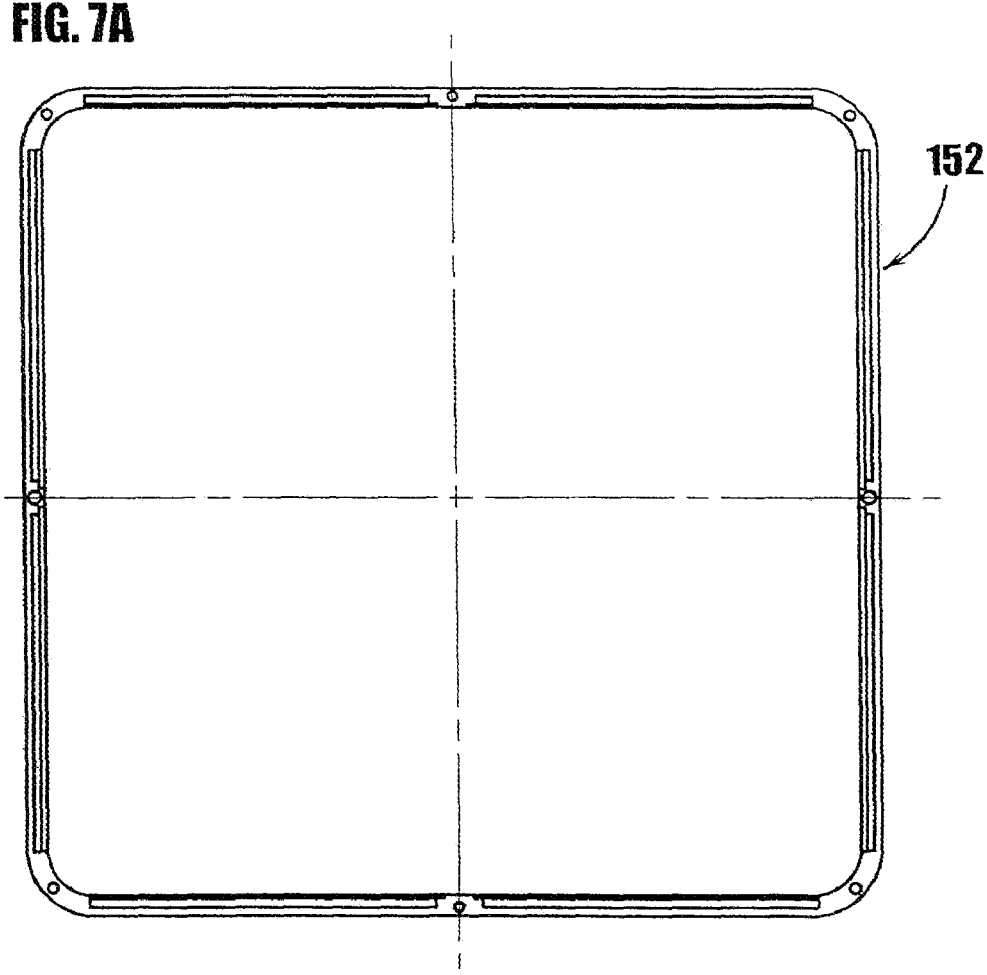

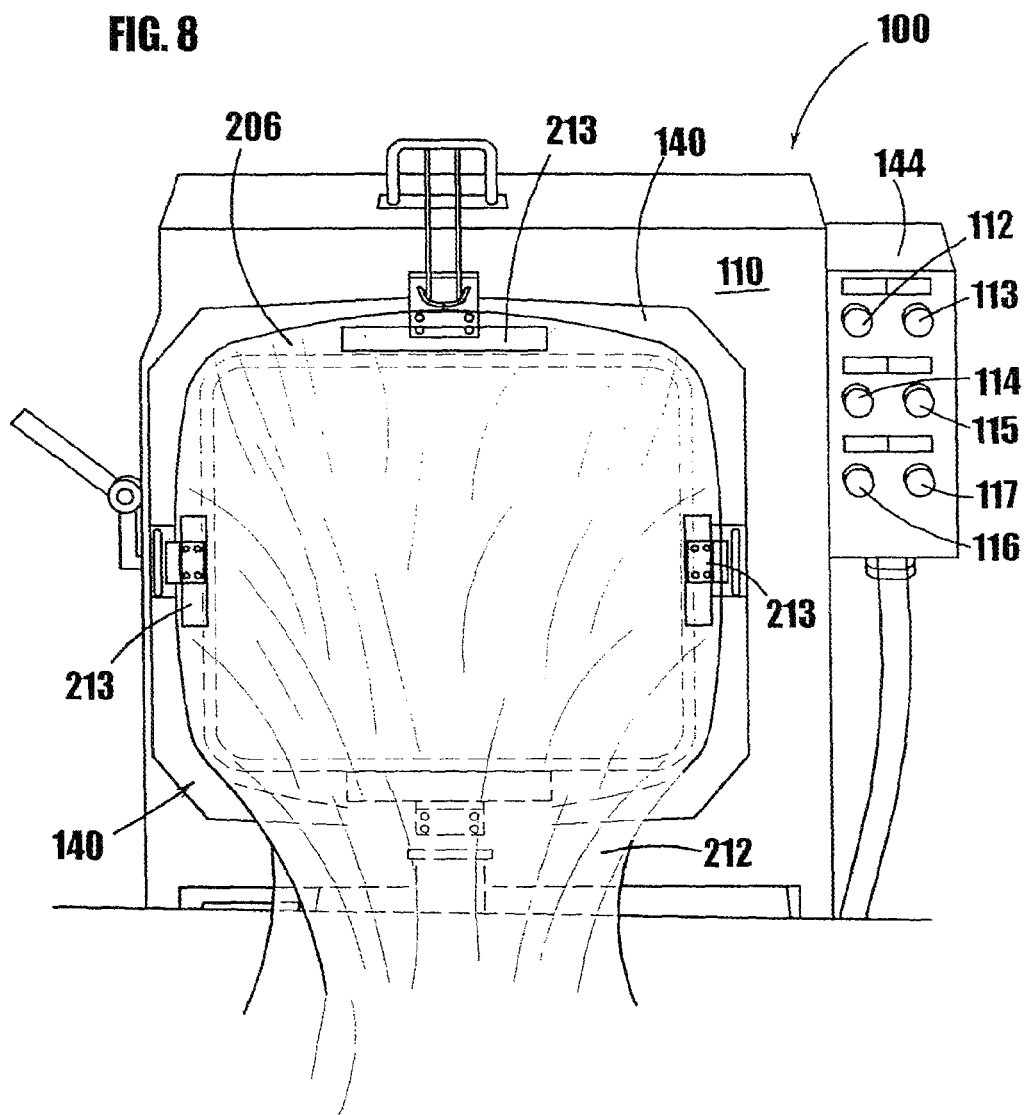

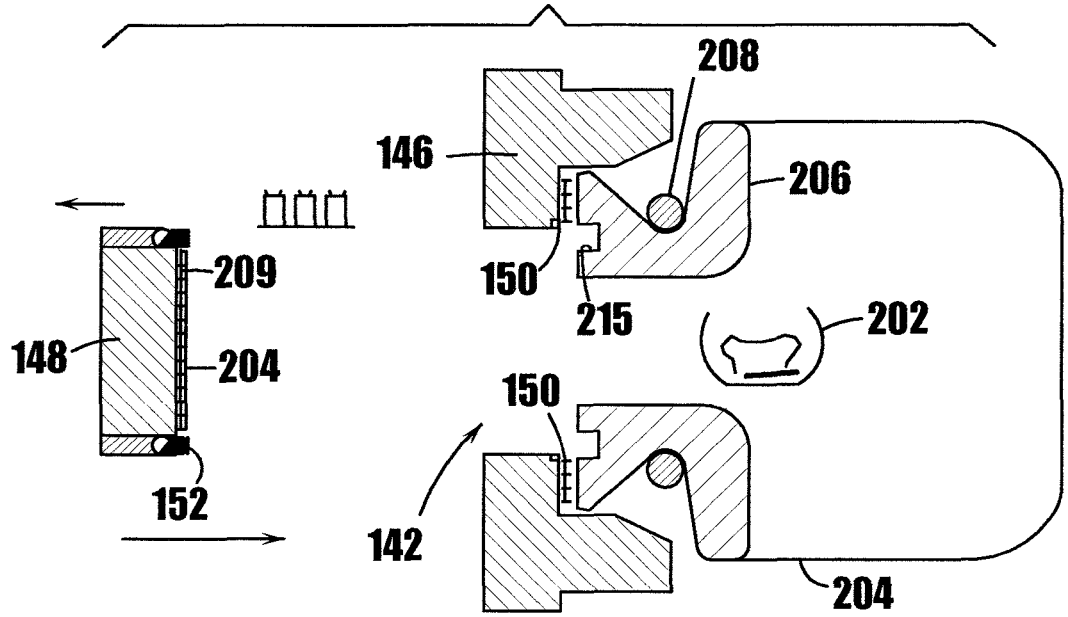
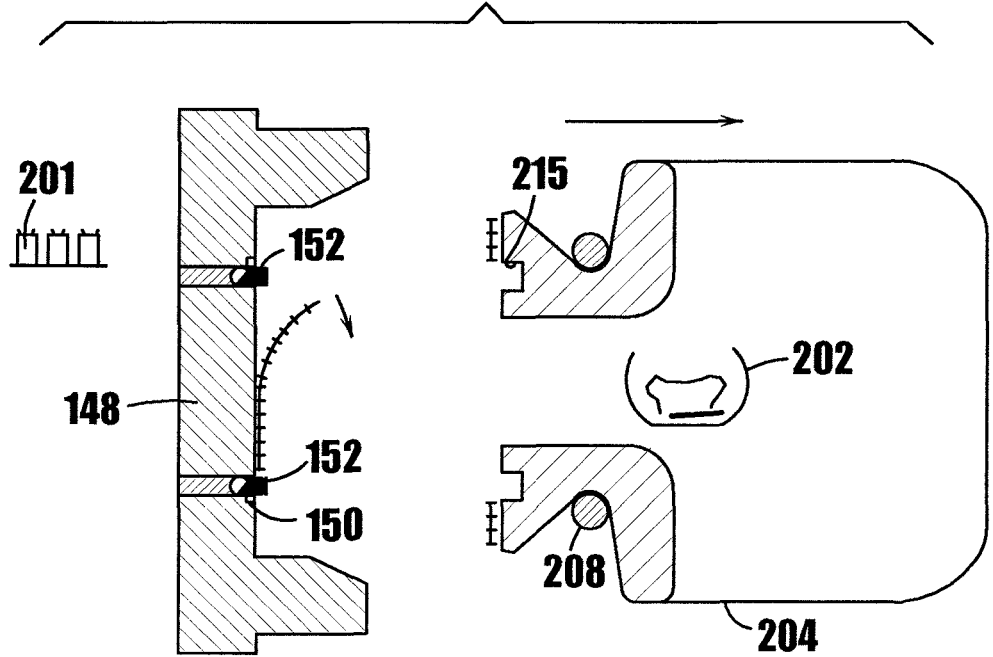

TRANSFER PORT AND METHOD FOR TRANSFERRING STERILE ITEMS

CROSS-REFERENCE TO RELATED APPLICATION

This patent application is a divisional of U.S. patent application Ser. No. 10/241,249, filed Sep. 10, 2002, now U.S. Pat. No. 8,163,251, which claims priority to U.S. Provisional Patent Application No. 60/318,546, filed Sep. 10, 2001, both of which are incorporated herein by reference.

FIELD OF THE INVENTION

The subject invention relates to systems for bagging and transferring sterile items, and more particularly, to an apparatus for assembling a bag for receiving sterile items and a sterile transfer port for transferring the sterile items from the bag into a sterile environment.

BACKGROUND OF THE INVENTION

In many cases, such as the medical, pharmaceutical, biological and food industries, it is desirable to transfer articles from one place to another, without the latter being subjected to the action of the atmosphere or to the environment in which the articles pass. An example of such a transfer of particular interest is the transfer of sterilized objects into a sterile enclosure. Another example is the transfer of articles in a certain gaseous atmosphere, for example nitrogen or argon, into an enclosure containing nitrogen or argon, whilst passing through a normal atmosphere.

In view of the above, several systems have been developed to guaranty absolute protection of sterile items from the atmospheres through which they pass. This method should preferably be simple, inexpensive and effective. For example, U.S. Pat. No. 5,816,772 to Py, incorporated herein by reference, discloses a method of transferring items into a receiving enclosure. The articles are contained in a transfer pocket. The transfer pocket has a rigid portion which is rendered adhesive. The adhesive secures the transfer pocket to a window. The window is removably attached within a frame of the enclosure by latches. When the transfer pocket is attached to the window, heating blades can spring out to cut a hole in the transfer pocket. Subsequently, the window is removed and retains the excised portion. As a result, the items can be transferred into the enclosure. However, this system may not provide complete protection from contamination during the transfer because a ring of internal pocket remains between the cutting element and the frame. This ring may cause undesirable contamination. Further, the excised portion attached to the window may be another source of contamination within the enclosure.

The subject disclosure provides a transfer port that overcomes such undesirable sources of contamination as well as an apparatus for assembling a bag with the necessary features. These and other unique features of the apparatus and method disclosed herein will become more readily apparent from the following description, the accompanying drawings and the appended exemplary claims.

SUMMARY OF THE INVENTION

The present invention is directed to a transfer port for the passage therethrough of articles sealed within a container. The transfer port includes a frame defining a transfer opening and a first heating element extending about the transfer opening. A door moves between an open position spaced away from the transfer opening for allowing the passage of articles therethrough, and a closed position covering the transfer opening for forming a substantially hermetic seal between the door and frame and for preventing the passage of articles therethrough. A second heating element extends about a peripheral portion of the door. The second heating element is movable relative to the first heating element and is engageable with a portion of the article container overlying the transfer opening for heating and excising the portion from the remainder of the container and, in turn, allowing the passage of articles from the container through the transfer opening. The first and second heating elements are preferably substantially contiguous to each other with the door in the closed position and the first heating element defines a ring of concern about the periphery of the transfer opening.

In a currently preferred embodiment of the present invention, the article container includes a bag having a mounting member defining a peripheral portion secured to the bag and a second transfer opening formed therethrough. An adhesive is superimposed over a portion of the bag overlying the second transfer opening of the mounting member and a releasable backing is superimposed over the adhesive.

The present invention also is directed to an apparatus for assembling the article container having a first support for supporting thereon a mounting member of the article container, and a second support for supporting thereon a bag or other suitable container with one wall of the bag located on one side of the mounting member and another wall of the bag located on an opposite side of the mounting member. A third support of the apparatus is spaced relative to the second support and includes a first support surface releasably supporting thereon at least one, and preferably a plurality of fasteners. In a currently preferred embodiment of the present invention, the fastener is an elastic ring. At least one of the second and third supports is movable relative to the other for tensioning a wall of the bag over the mounting member and applying the fastener thereto to secure the respective wall of the bag to the mounting member in a taut condition. The third support further includes a second support surface releasably supporting thereon the releasable backing and adhesive underlying the releasable backing. The adhesive is engaged with the bag by moving the second and third supports together to, in turn, adhesively secure the adhesive and releasable backing to the bag. Preferably, the second support surface of the third support is coupled to a vacuum source for drawing a vacuum through the second support surface and, in turn, selectively securing the releasable backing and underlying adhesive thereto.

One advantage of the present invention is that it maintains a ring of concern about the transfer opening that prevents migration of contaminants into the sterile environment of the transfer port. Other advantages of the present invention will become more readily apparent in view of the following detailed description of preferred embodiments and accompanying drawings.

BRIEF DESCRIPTION OF THE DRAWINGS

So that those having ordinary skill in the art to which the disclosed apparatus and method appertain will more readily understand how to make and use the same, reference may be had to the drawings wherein:

FIG. 4A illustrates a side view cross-section of the transfer port of the enclosure system of FIG. 1;

FIG. 6A illustrates a front view of the "watchdog" or outer heated element of the transfer port of the enclosure system of FIG. 1;

FIG. 6B illustrates a top view of a heat element for a transfer port of the enclosure system of FIG. 1;

FIG. 6C illustrates an enlarged view of area C of FIG. 6B;

FIG. 7A illustrates a front view of the inner or door heated element of the transfer port of the enclosure system of FIG. 1;

FIG. 7B illustrates a top view of the inner or door heated element of the transfer port of the enclosure system of FIG. 1;

FIG. 7C illustrates an exploded view of area C of FIG. 7B;

FIG. 8 illustrates the transfer port of the enclosure system of FIG. 1 with a sterile bag attached thereto;

FIG. 29 illustrates a cross-sectional view of an open transfer bag system mounted to the enclosure system of FIG. 1 for receiving debris from the enclosure system; and FIG. 30 illustrates a cross-sectional view of an open transfer bag system after removal from the enclosure system of FIG. 1.

DETAILED DESCRIPTION OF EMBODIMENTS OF THE INVENTION

Figure 1:
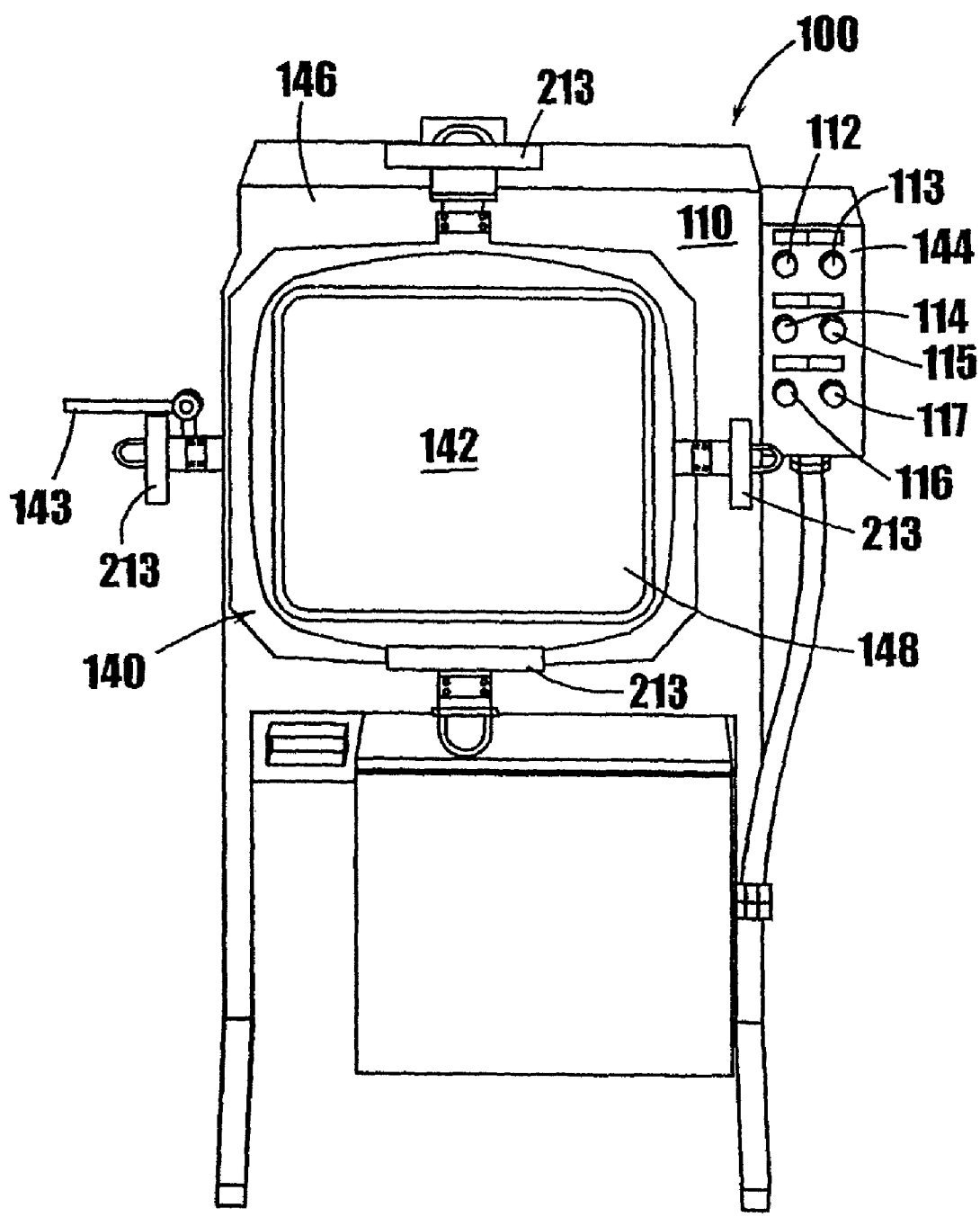
FIG. 1 illustrates a front view of an enclosure system constructed in accordance with a preferred embodiment of the subject disclosure.

The present invention overcomes many of the prior art problems associated with transferring sterile items. The advantages, and other features of the systems and methods disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Figure 2:
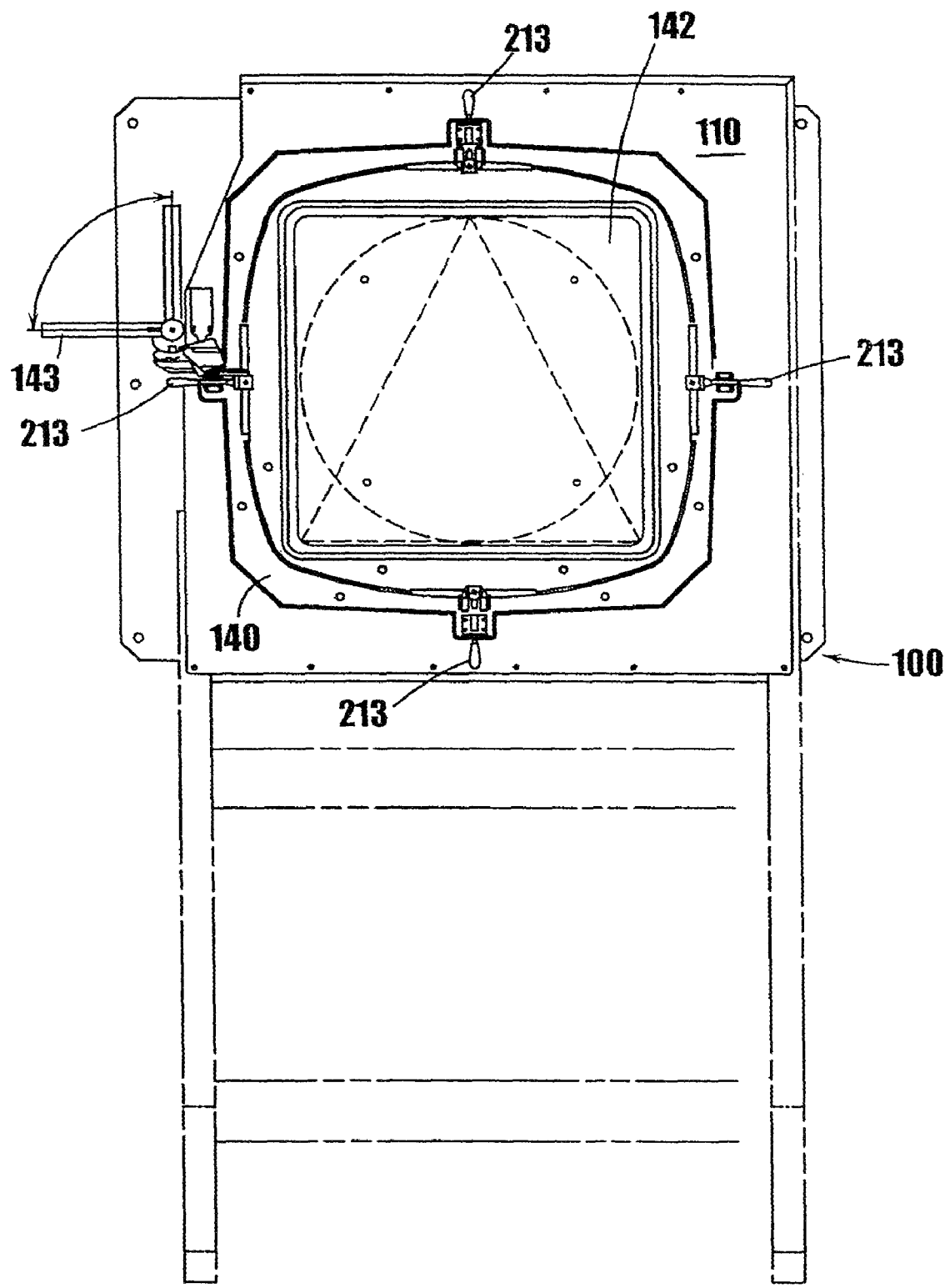
FIG. 2 illustrates a transfer port for transferring sterile items from a sterile bag to the enclosure system of FIG. 1.
Figure 3:
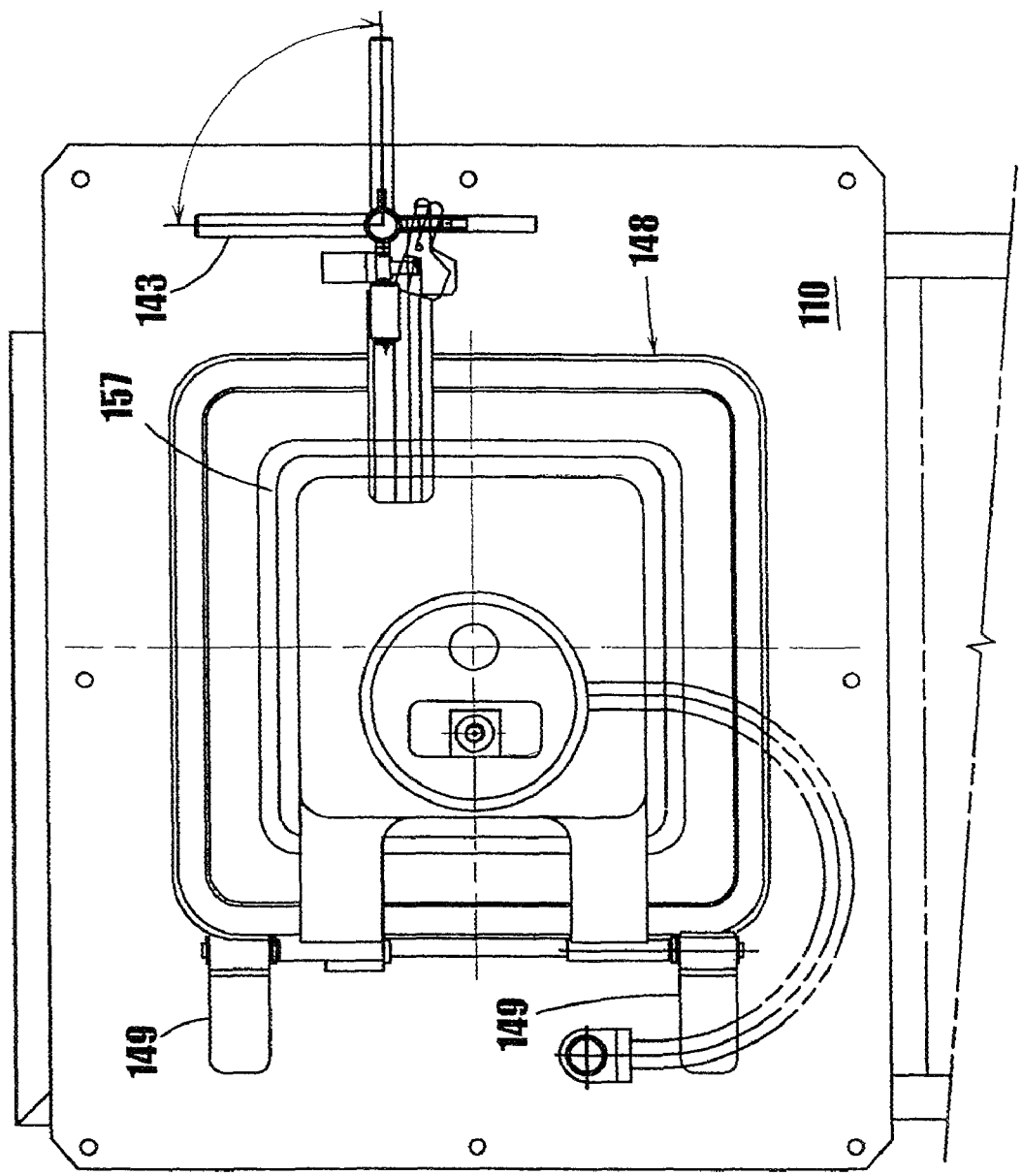
FIG. 3 illustrates an interior view of the transfer port for transferring sterile items from a sterile bag to the enclosure system of FIG. 1.

Referring to FIGS. 1 and 2, the enclosure 100 into which the sterile items 201 (FIG. 9) are transferred is preferably any protected or decontaminated enclosure, such as a sterile enclosure, and preferably an enclosure of Class 10 level or better. Such an enclosure 100 contains a controlled atmosphere and in the currently preferred embodiment is provided with laminar flow. The enclosure 100 includes an access wall 110 having a recess for receiving a transfer port or module 140. The transfer module 140 includes a window 142 for transferring items 201 (FIG. 9) into the enclosure 100. Window 142 is understood to refer to an element of the enclosure 100, articulated or not articulated, capable of efficiently and hermetically obturating the corresponding opening for the purpose of constituting an effective barrier against the external atmosphere, in particular against microorganisms. A door assembly or port 148 covers the window 142 to maintain the inside of the enclosure 100 as a sealed environment. Preferably, the port 148 pivots to an open position by hinges 149. In an alternate embodiment, the port 148 moves back beyond the window 142, then rotates to expose the window 142. A handle 143 is provided for locking and unlocking the port 148. Thus, the required space for the port 148 motion is minimized and the sterile area within the enclosure 100 is maximized. Further, laminar air flow can be increased when the window 142 is open to further ensure adequate protection against unwanted migration of contaminants.

Figure 23:
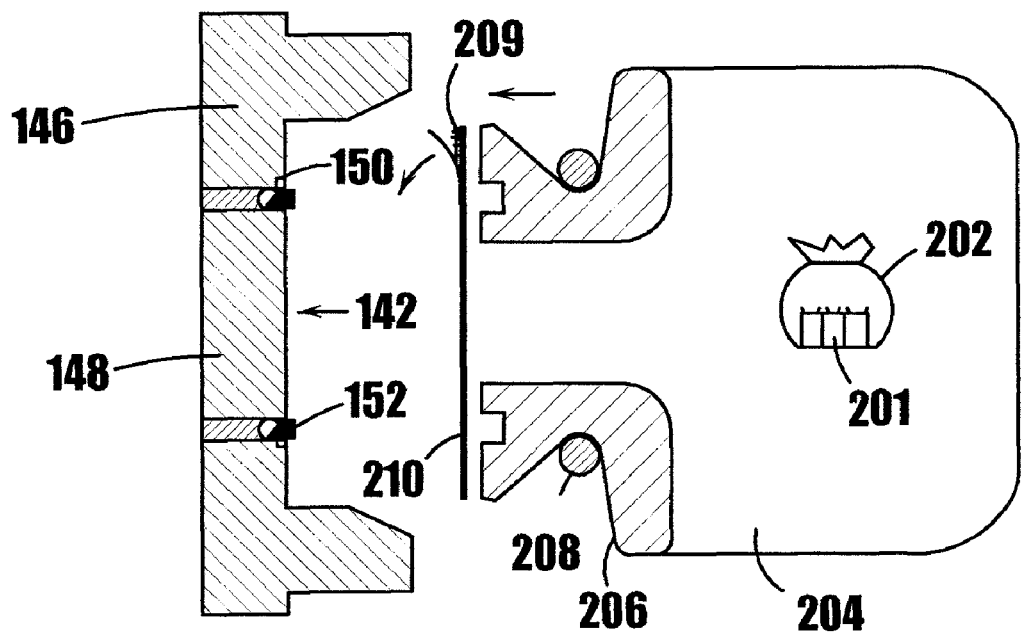
FIG. 23 illustrates a cross-sectional view of a transfer bag system prior to mounting to the enclosure system of FIG. 1.

An actuating mechanism 144 is coupled to the port 148 to allow opening and closing of the port 148. The status of the port 148 and various other parameters are indicated on the actuating mechanism 144 as well. In a preferred embodiment, the actuating mechanism includes button 112 for powering the enclosure 100, a button 113 for indicating defective alignment, a button 114 to begin an operational cycle, a button 115 to open the port 148, a button 116 to start an operational cycle and a button 117 to stop an operational cycle. The enclosure 100 also includes a control module 160 for maintaining the parameters within the enclosure 100, supplying power to the transfer module 140 and the like. Preferably, a table (not shown) is positioned outside the transfer module 140 to provide a surface for resting a transfer bag system 200 (FIG. 9) during transfer of items 201 from the bag system into the enclosure 100. During operation, and as described further below, a sterile bag assembly 200 is placed on the table and a portion thereof is affixed to the port 148 by an adhesive 209 (FIG. 23).

Figure 4B:
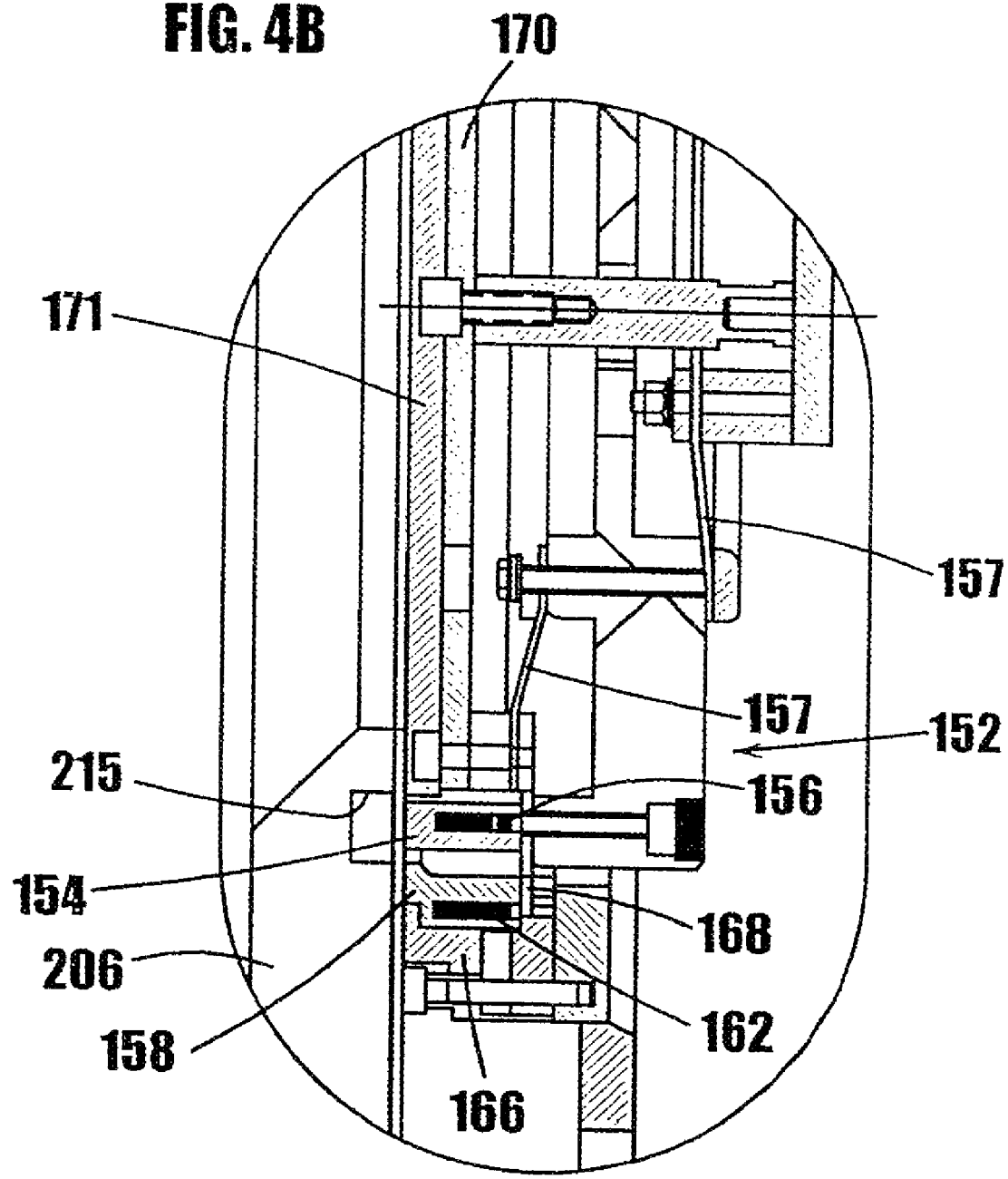
FIG. 4B illustrates an exploded view of area B of FIG. 4A.
Figure 5:
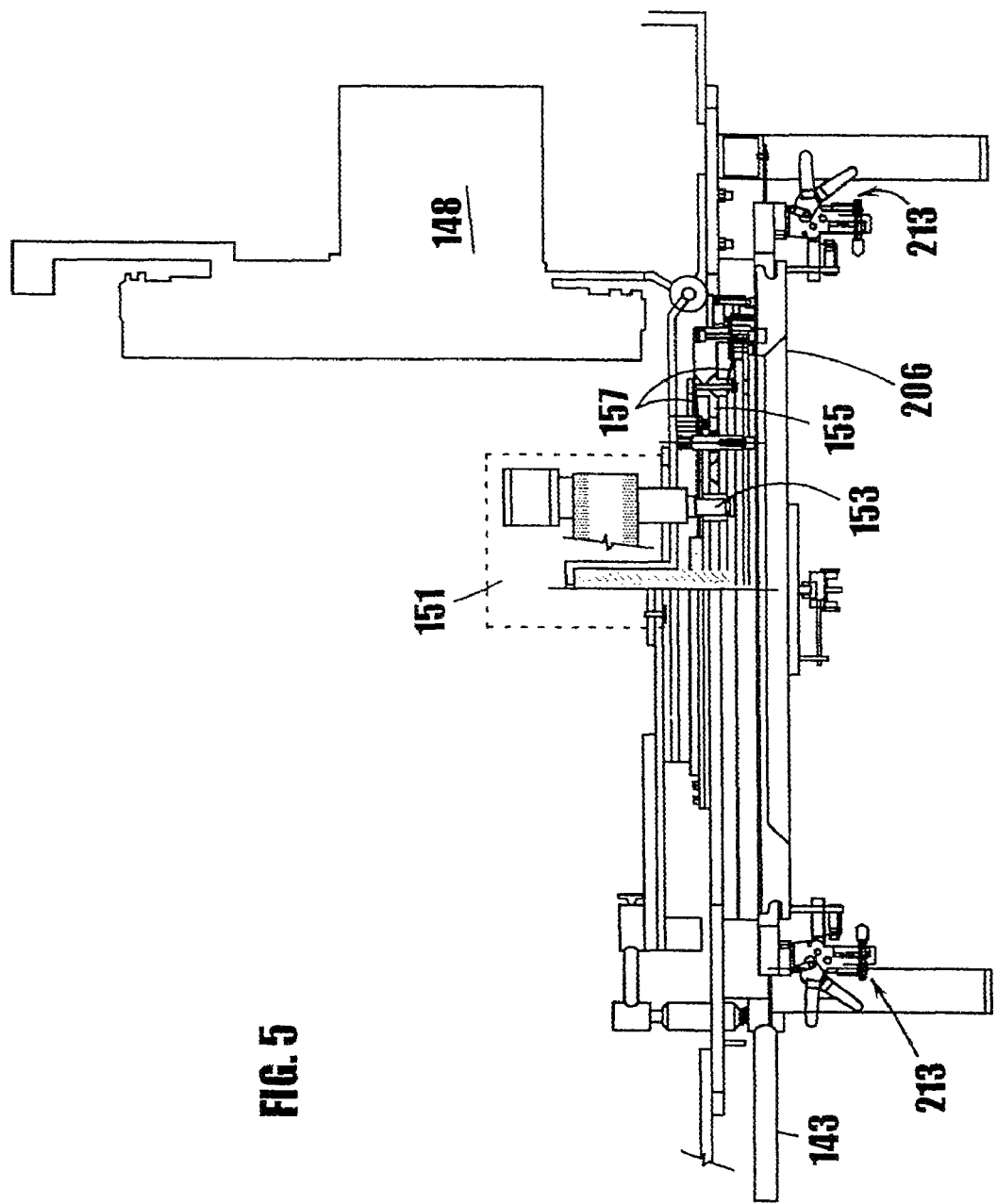
FIG. 5 illustrates a top view cross-section of the transfer port of the enclosure system of FIG. 1.
Figure 9:
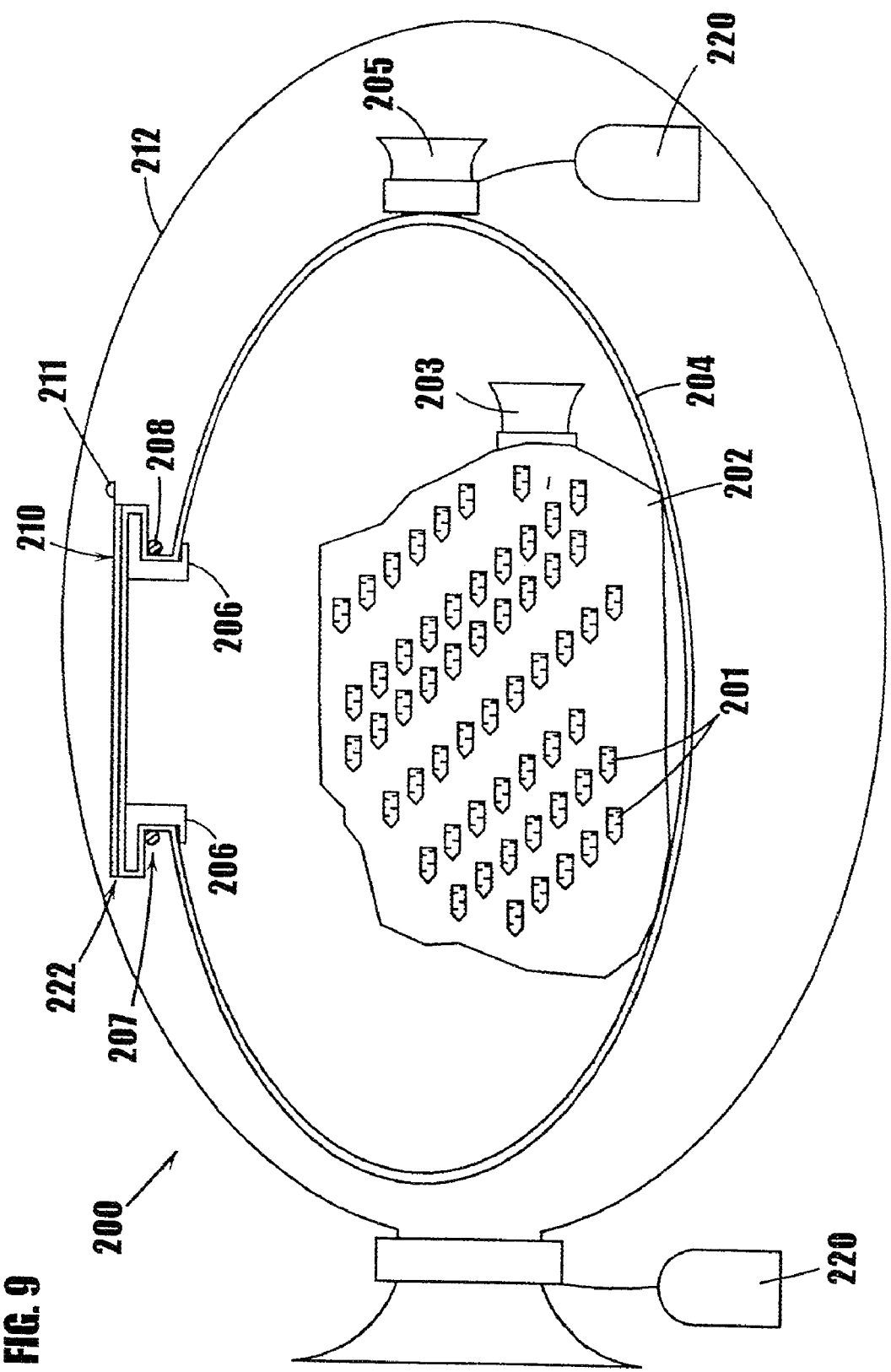
FIG. 9 illustrates in cross-section a transfer bag system constructed in accordance with the subject disclosure.
Figure 10:
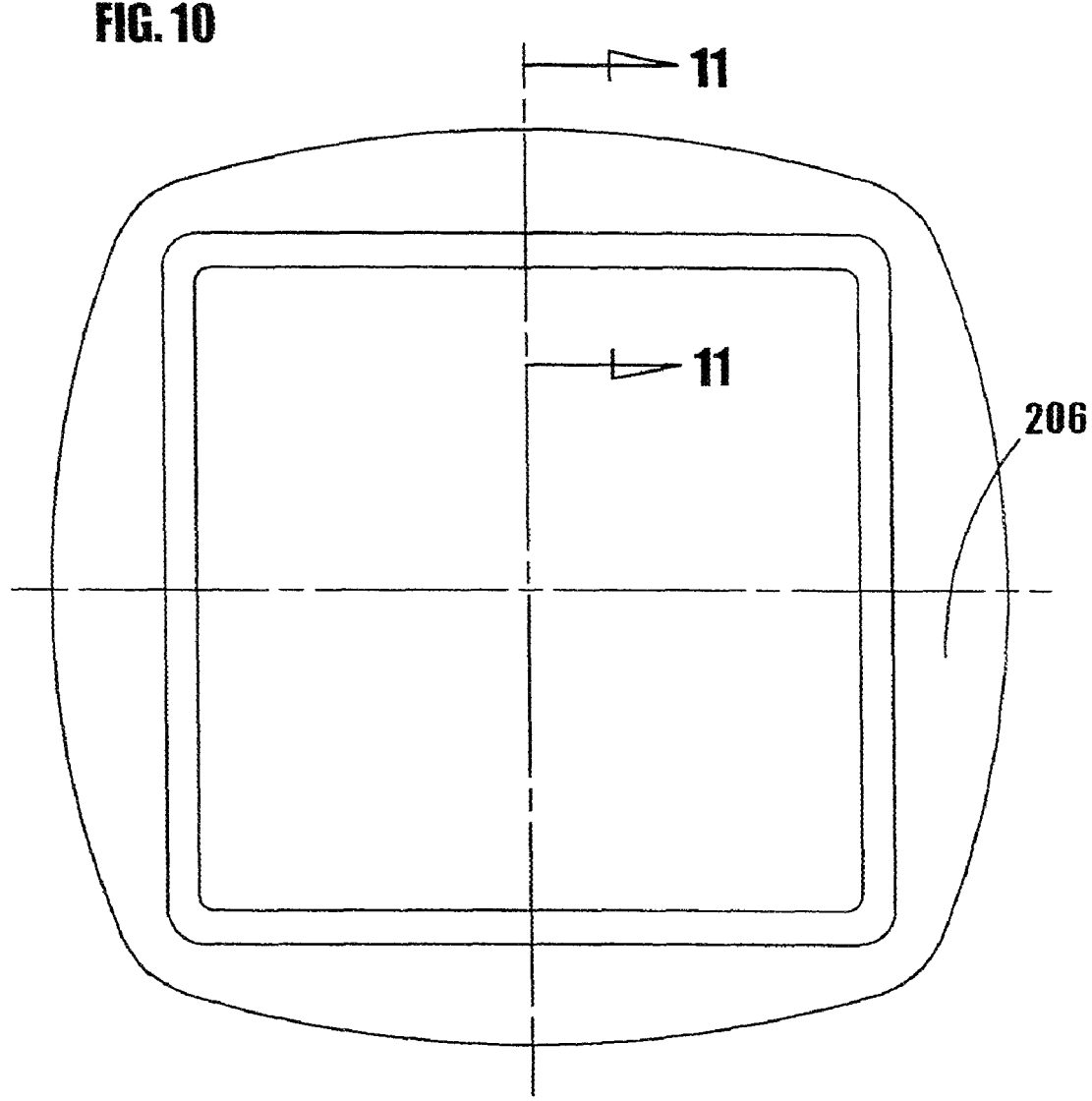
FIG. 10 illustrates a front view of a tambourine or mounting member for the transfer bag system of FIG. 9.
Figure 11:
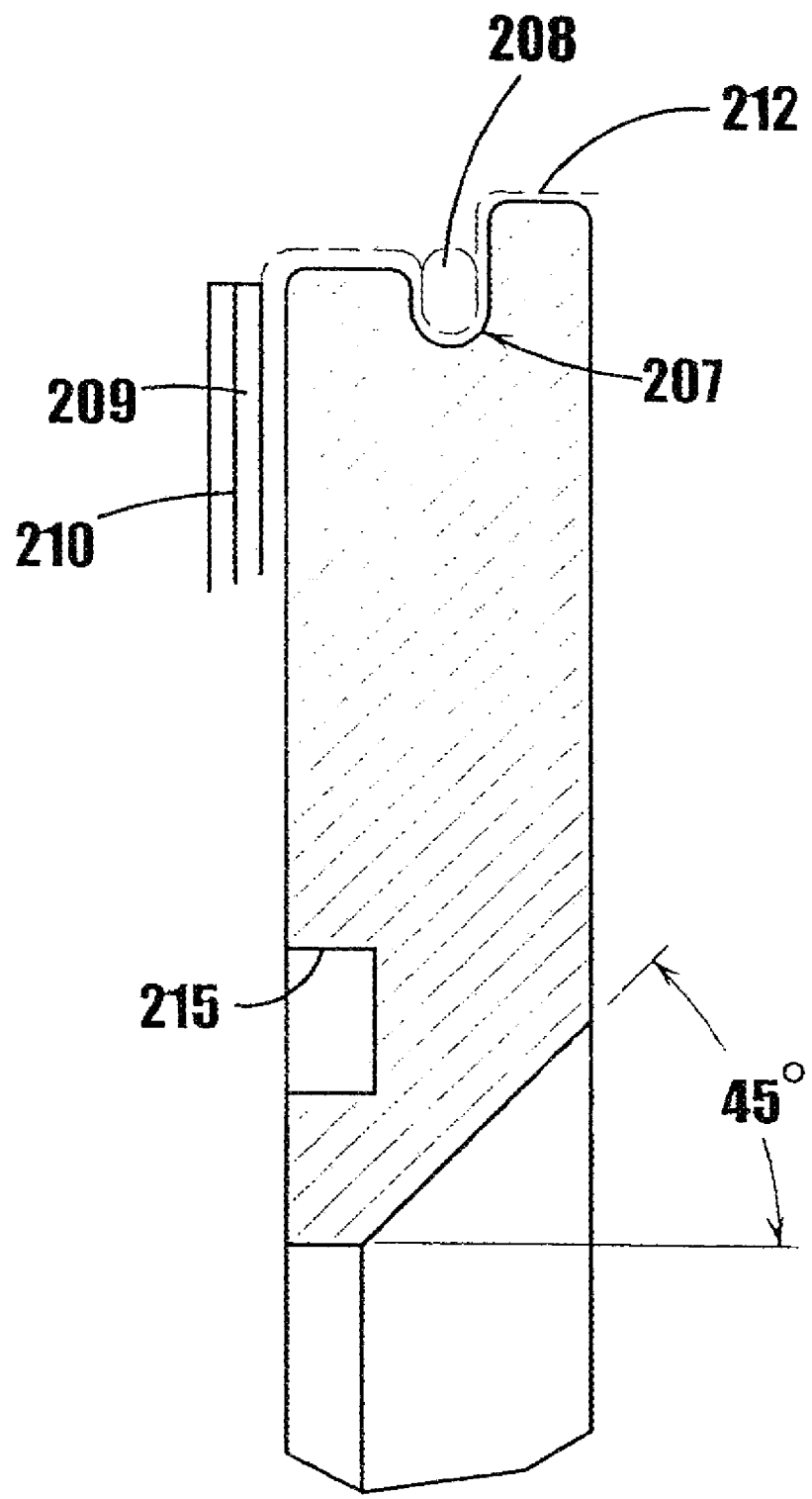
FIG. 11 illustrates in cross-section of the tambourine of FIG. 10.

The transfer module 140 defines the window 142 and mounts within an opening defined by the access wall 110 of the enclosure 100. It is envisioned that the window 142 may be rectangular for transferring boxes, circular as shown in dashed lines on FIG. 2, triangular as shown in dashed lines on FIG. 2, or any shape as may be appropriate for the application. Referring to FIGS. 7A-C, the heated cutting element assembly 152 mounted on the port 148 serves to sterilize and sever a portion of a sterile bag 204 (FIG. 9). As shown best in FIGS. 23-30, the heated cutting element 152 preferably slides outward to contact and sever a portion of the transfer bag assembly 200. As shown in FIGS. 7A-7C, the heated cutting element 152 has a blunt rectangular shape to not only effectively sever but sterilize a large area during operation. Alternatively, the heated cutting element may define an angled cutting surface, in a cutting surface defining another desired shape. In a preferred embodiment, the heated cutting element 152 is an element 154 with a plurality of heaters 156 attached thereto. Preferably, the heaters 156 are ceramic and capable of reaching an operating temperature of at least about 240 degrees C. as is available from Victon Technology Electronic Ltd of Guang-Dong, China. The heaters 156 are controlled by the control module 160. Preferably, the excised portion of the sterile bag assembly 200 remains affixed to the port 148 for subsequent removal. A drive mechanism 151 (FIG. 5) operatively associated with the heated cutting element 152 controls the position of the cutting element 152. A drive shaft 153 coupled to a support 155 connects the heated cutting element 152 to the drive mechanism 151. The support 155 moves between extended and retracted positions to, in turn, move the heated cutting element 152 between extended and retracted positions along arrow "A" shown in FIG. 4B. As the drive mechanism 151 actuates, particles, lubricant or other contaminants may be generated. In order to prevent migration of such contamination into the enclosure 100, diaphragms 157 are provided to allow for movement and maintain a barrier between the drive unit 151 and interior of the enclosure 100.

A window heating element assembly 150 is mounted about the window 142 in order to sterilize a ring of concern and prevent migration of contaminants into the interior of the enclosure 100. It will be appreciated upon review of the subject disclosure by those of ordinary skill in the pertinent art that the ring of concern may be rectangular, circular, triangular, or other suitable configuration as appropriate or desired. Preferably, the cutting element 152 defines the periphery of the port 148 and the window heating element 150 defines the periphery of the window 142. Thus, the heated cutting element 152 and the window heating element 150 are substantially contiguous during severing of the transfer bag system 200. The close proximity of the cutting element 152 and the window heating element 150 effectively sterilizes the area therebetween.

Referring to FIGS. 4A, 4B, 5 and 6A-C, the heating element 150 includes a heating element 158 which is heated by a plurality of heaters 162. Preferably, the heaters 162 are ceramic and capable of reaching an operating temperature of at least about 240 degrees C. as is available from Victon Technology Electronic Ltd of Guang-Dong, China. The heaters 162 are controlled by the control module 160. The window 142 defines a space 164 for wires (not shown) to interconnect the heaters 162. Tape (not shown) as well as insulation 166 serves to retain the heaters 162. Preferably, the insulation 166 and heating elements have a TEFLON® ceramic reinforced coating or other suitable abrasion resistant, excellent release coating which can be applied as necessary. As may be recognized by those of ordinary skill in the pertinent art, any of numerous different non-stick coatings that are currently available or later developed equally may be used.

In a preferred embodiment, the door 148 is made of an insulating material to prevent heat sinking and decrease the heat-up time of the cutting element 152 and heating element 150. Accordingly, the time required for the cutting element 152 and heating element 150 to reach the operational temperature is minimized. In another embodiment, the port 148 has vents for removing particulates generated during the cutting of the intermediate bag 204 so no foreign mater, organic or inorganic, enters the sterile side of the port 148. A resilient seal 168 insures a hermetic closure when the door 148 is in the closed position. The door 148 has a backing plate 170 to provide structural support and rigidity. The outside plate 171 of the door 148 is preferably coated with a TEFLON® ceramic reinforced coating to facilitate easy removal of adhesive tape and any portion of the sterile bag 204 which may become burned thereon. As may be recognized by those of ordinary skill in the pertinent art, any of numerous different non-stick coatings that are currently available or later developed equally may be used.

Referring to FIG. 9, the transfer bag system 200 includes three distinct transfer bags. The sterile items 201 to be transferred, in this case vials, bottles, or other sterile devices or containers, are enclosed in an inner bag 202 whose opening 203 has been obturated. The inner bag 202 enclosing the items 201 is placed in an intermediate bag 204 whose opening 205 has been obturated and provided with a sterilization indicator 220. A frame or tambourine 206 defines a flat portion having a peripheral groove 207 in which a portion of the intermediate bag 204 is retained by means of an elastic band 208. Thus, the structure of a diametrical cross section of the frame 206 has the general shape of a "U" of which one of the sides is shorter than the other resulting in the outer surface of the intermediate bag 204 having an "S" shape. On the "S" part 222 of the intermediate bag 204, held by the frame 206, there is placed an adhesive 209 protected by a protective film 210 provided with a tab 211. The frame 206 also defines a groove 215 for receiving the heated cutting element 152 in the extended position. The frame 206 and the articles enclosed in the inner bag 202 were of course placed inside the closed intermediate bag 204 before the intermediate bag 204 was closed. The inner bag 202 and the intermediate bag 204 have themselves been placed inside an outer bag 212, which is closed. The outer bag 212, like the others, may be provided with a sterilization indicator 220 and with identification devices such as bar codes.

Preferably, each envelope of the transfer bag system 200 is a flexible or semi-rigid bag essentially formed from an envelope. The transfer bags can be of any nature adapted to protect the articles to be transferred from the action of the atmosphere or atmospheres which the latter have to pass through. The more particularly chosen bags are those whose nature is such that the bag can be exposed to gamma, e-beam, or other radiation for the purpose of obtaining the sterility of the contents of the transfer bag whilst protecting the contents from contamination after the action of the radiation. Transfer bags are also chosen whose nature is permeable to the action of ethylene oxide. Transfer bags are preferably made from a plastic material like those used, for example, for packaging sterile articles such as probes, syringes, needles and the like which are particularly suitable for sterilization by gamma, e-beam or other radiation. However, as may be recognized by those of ordinary skill in the pertinent art based upon the teachings herein, the transfer bags may take the form of any of numerous other types of enclosures, and may have walls that are flexible, semi-rigid, or rigid.

Referring to FIGS. 12-16, an apparatus for assembling the transfer bag system 200 is referred to generally by reference numeral 300. The apparatus 300 includes a frame 302 having a mount support 304 thereon for receiving and supporting a mounting member or tambourine 206 for attachment to a bag. A bag support 306 surrounds the mount support 304 for supporting thereon a bag to be attached to the mount 304 such that one wall of the bag is supported on one side of the tambourine 206 and another wall of the bag is located on an opposite side of the tambourine 206. An elastic fastener mount assembly 308 is spaced relative to the bag support 306 and includes a first support surface 310 for releasably supporting thereon at least one, and preferably a plurality of elastic fasteners 208. As described above, in the currently preferred embodiment of the present invention, the fasteners 208 are in the form of elastic bands, such as o-ring type elastic bands. However, as may be recognized by those of ordinary skill in the pertinent art based on the teachings herein, the fasteners 208 may take any of numerous different configurations that are currently, or later become known for performing the functions of the fastener 208.

The mount support 304 is movable vertically in the direction of arrow "B" (FIG. 12) toward and away from the elastic fastener mount 308 by actuation of a first manual lever 312 connected thereto by a linkage 311. As described further below, the first lever 312 is manipulated to move the mount support 304 upwardly, or toward the fastener mount 308 to, in turn, tension the bag thereon and facilitate applying the elastic band 208 to secure the bag to the tambourine 206. The elastic fastener mount 308 also is movable vertically, or toward the mount support 304 in the direction of arrow "B" (FIG. 12) by actuation of a second manual lever 313 connected to the frame and fastener mount by a linkage 315. As described further below, the second lever 313 is manipulated to move the fastener mount 308 downwardly into engagement with the tambourine 206 seated on the mount support 304 to apply a respective fastener 208 to the bag and tambourine to fixedly secure the tambourine to the bag, and to apply the adhesive 209 to the portion of the bag overlying the tambourine.

The elastic fastener mount 308 further includes on its underside a second support surface 314 for releasably supporting thereon an adhesive tape. In the currently preferred embodiment of the present invention, the adhesive tape is in the form of a releasable, protective film 210 adhered to an adhesive backing 209. The adhesive backing 209 is preferably double-sided foam tape that is engageable with the bag 204 on one side and retains a protective film 210 on the other side. In a preferred embodiment, the adhesive tape is SCOTCH® brand double-sided foam mounting tape available from the 3M Co. However, as may be recognized by those of ordinary skill in the pertinent art based on the teachings herein, this type of attachment mechanism is only exemplary, and any of numerous other types of adhesives or other attachment mechanisms that are currently, or later become known for performing the function of the adhesive 209 may be equally used.

Figure 12:
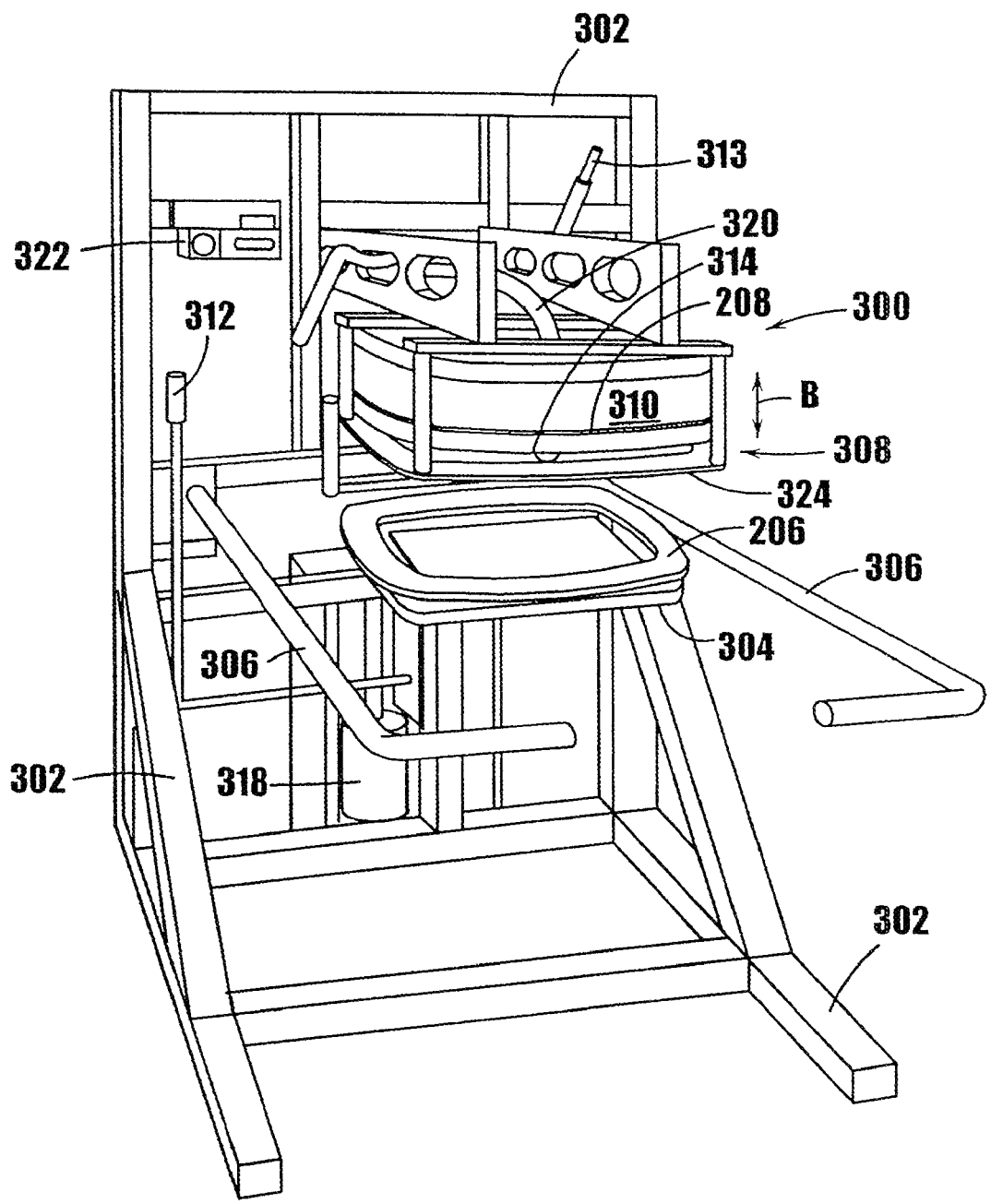
FIG. 12 illustrates a front perspective view of an apparatus for assembling a transfer bag constructed in accordance with a preferred embodiment of the subject disclosure.
Figure 13:
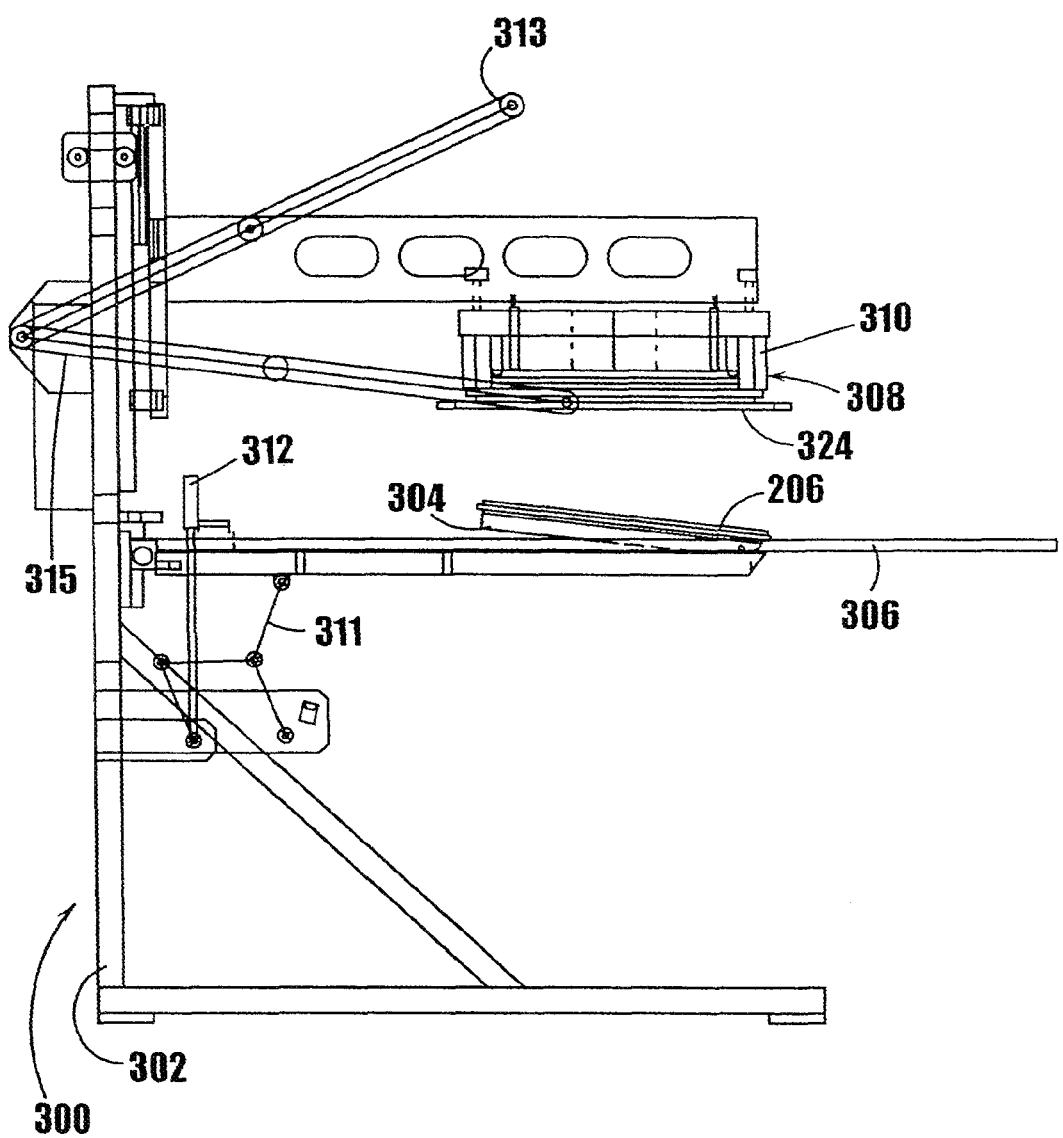
FIG. 13 illustrates a side view of the apparatus of FIG. 12.
Figure 14:
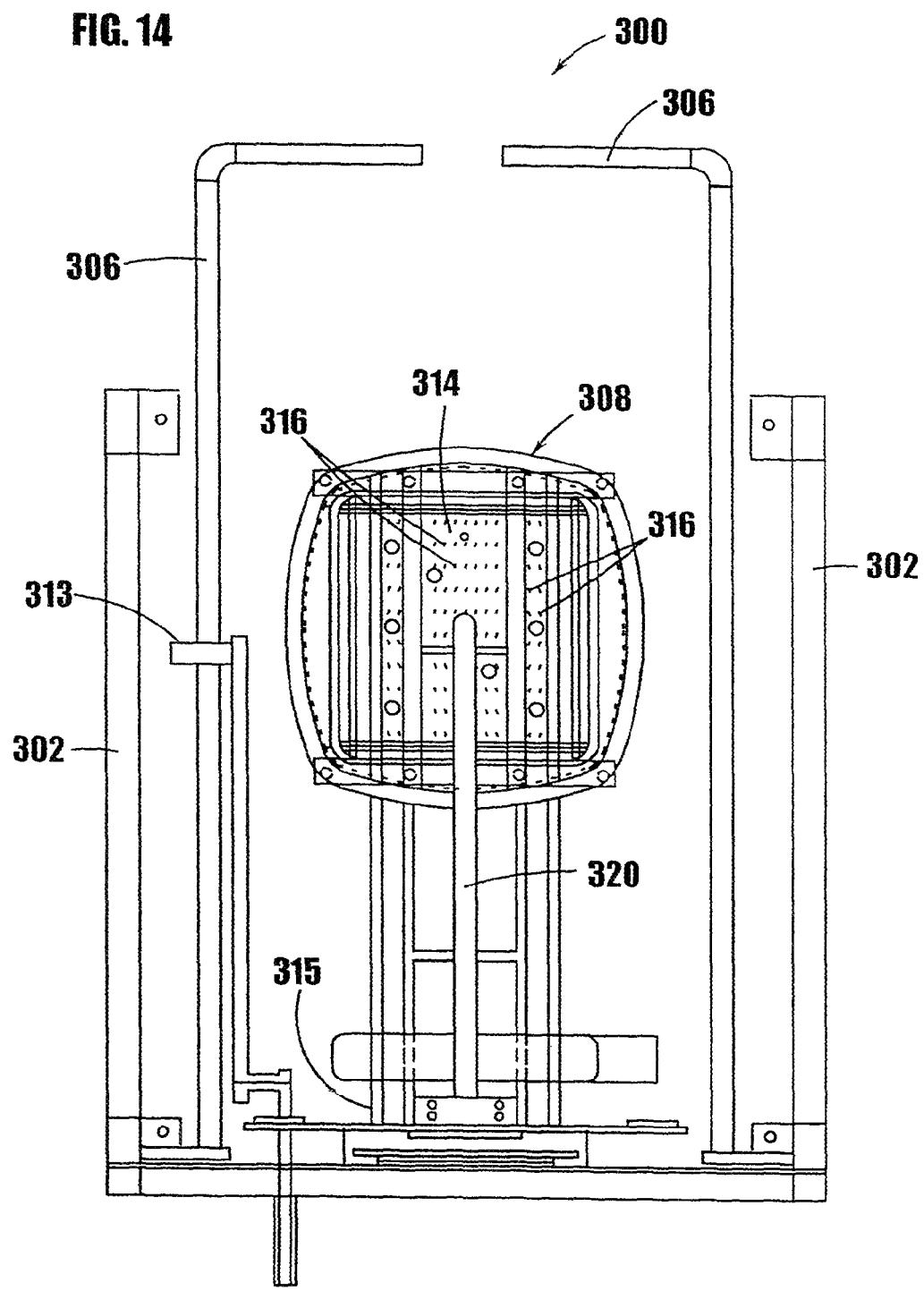
FIG. 14 illustrates a top view of the apparatus of FIG. 12.
Figure 15:
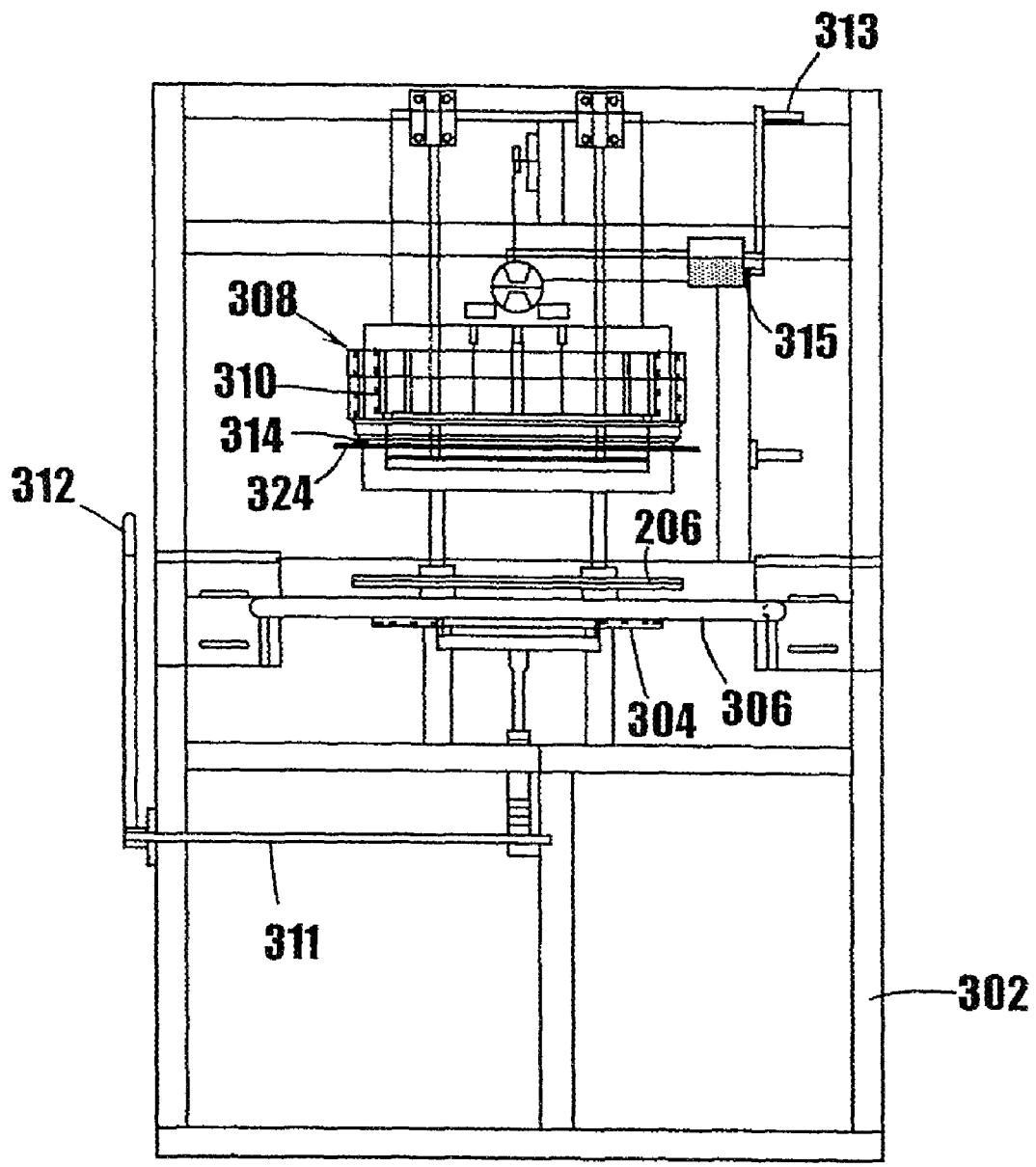
FIG. 15 illustrates a front elevational view of the apparatus of FIG. 12.
Figure 16:
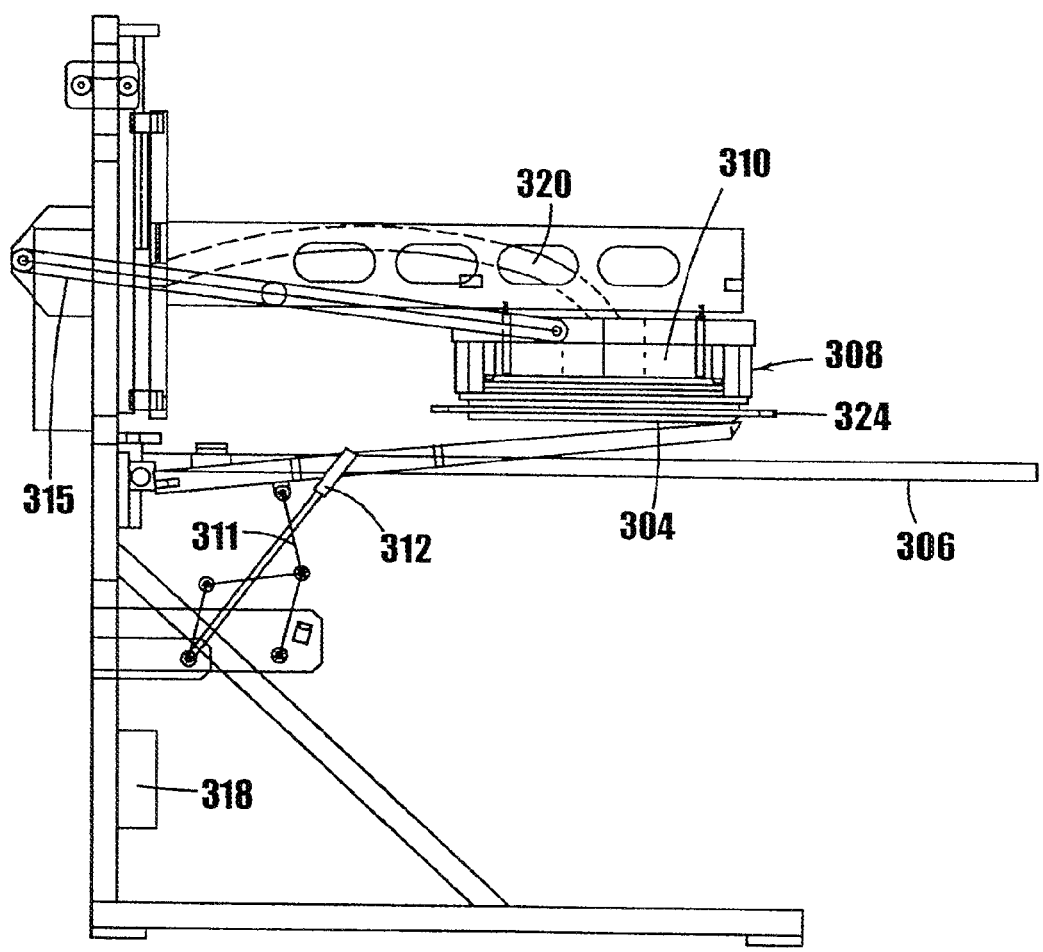
FIG. 16 illustrates a side view of the apparatus of FIG. 12 with the mount support engaged with the elastic fastener mount.

As shown in FIG. 14, the second support surface 315 of the fastener mount 308 is perforated and defines a plurality of vacuum apertures 316 therethrough. As shown in FIG. 12, the vacuum apertures 316 are coupled to a vacuum source 318 by vacuum lines 320. A control unit 322 is electrically connected to the vacuum source 318 and is operable to draw a vacuum through the vacuum lines 320 and vacuum apertures 316 of the second support surface 316 to, in turn, releasably secure the protective film 210 of the adhesive tape thereto.

The faster mount 308 further includes a tensioning flange 324 extending about the periphery of the fastener support surface 310. As can be seen, the tensioning flange 324 is spaced laterally outwardly and below the bottom edge of the first support surface 310 to engage and further tension the portion of the bag surrounding the tambourine to facilitate attachment of the adhesive and elastic fastener to the bag.

Figure 17:
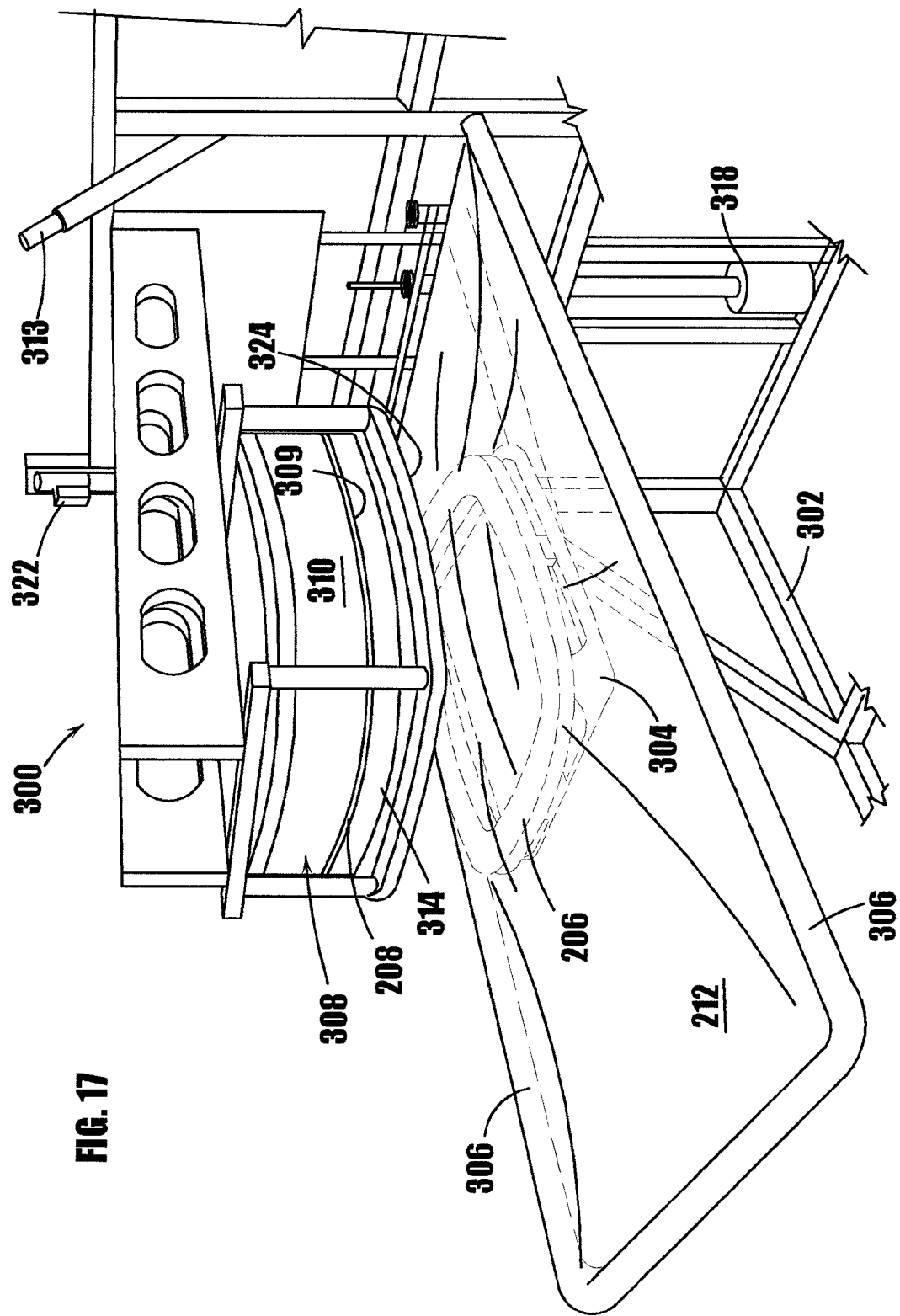
FIG. 17 is a side perspective view of the apparatus of FIG. 12 with a sterile bag mounted thereto.
Figure 18:
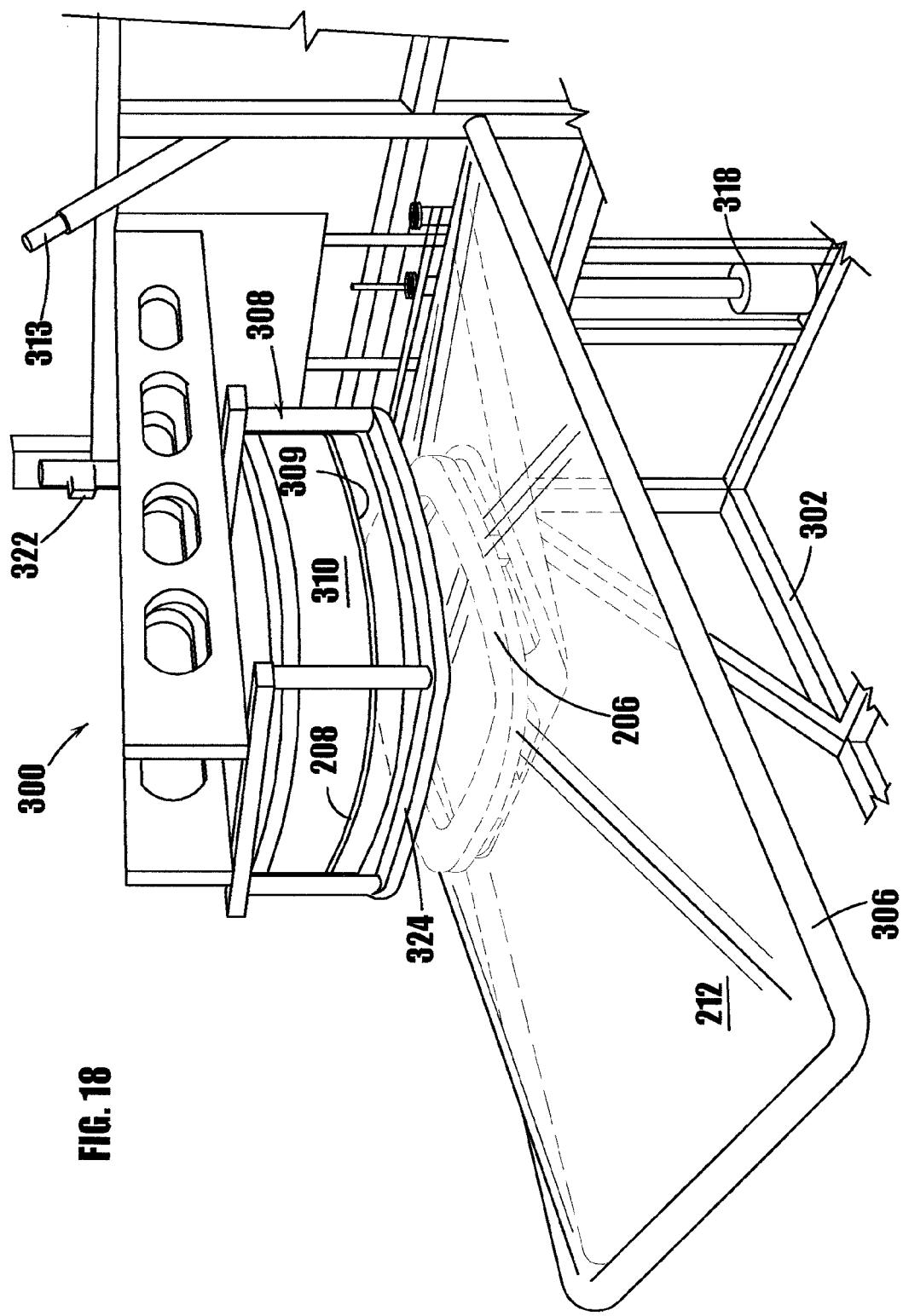
FIG. 18 is a side perspective view of the apparatus of FIG. 12 with the mount support tensioning the sterile bag.
Figure 19:
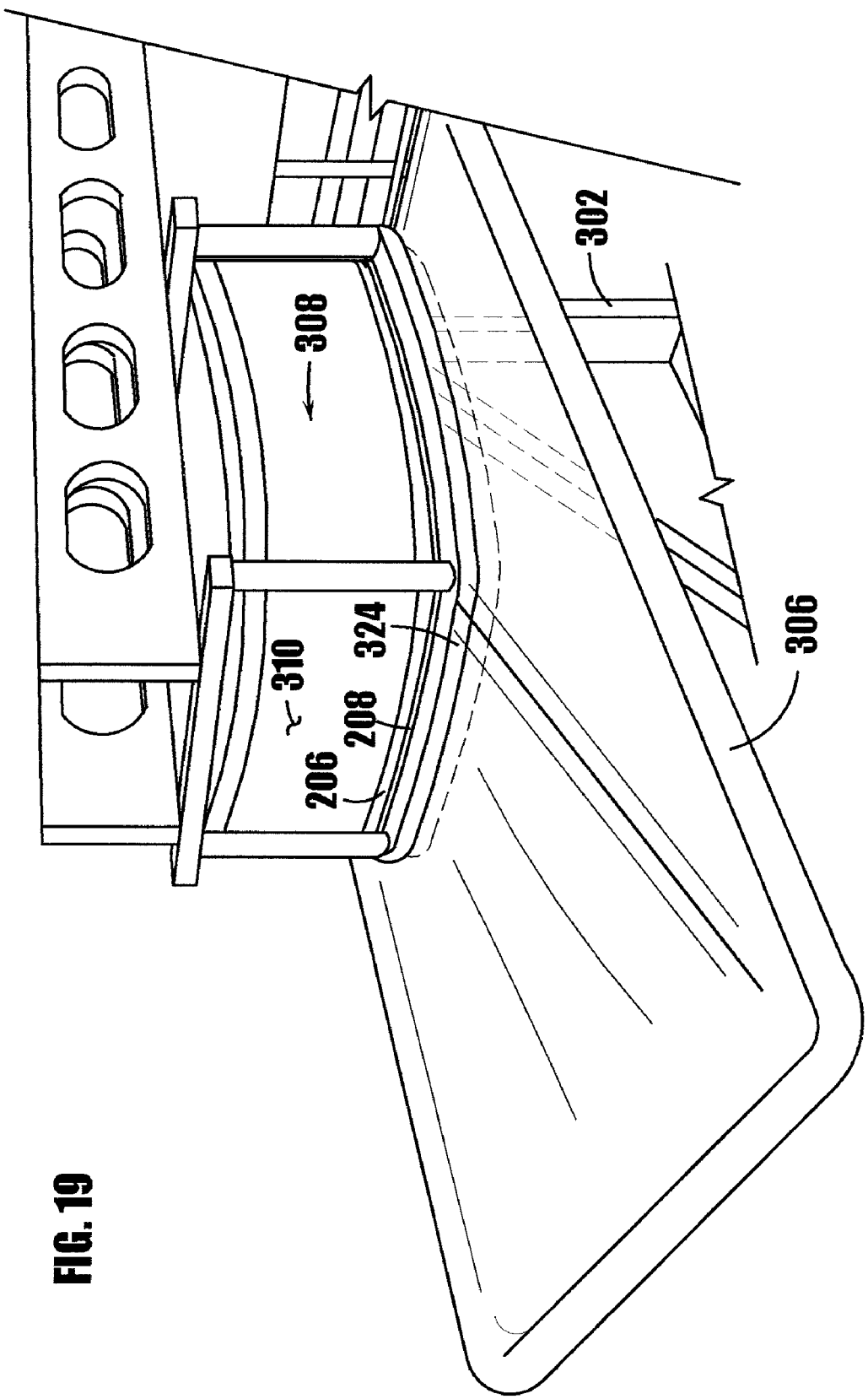
FIG. 19 is a partial, side perspective view of the apparatus of FIG. 12 with elastic fastener mount engaging the sterile bag.
Figure 20:
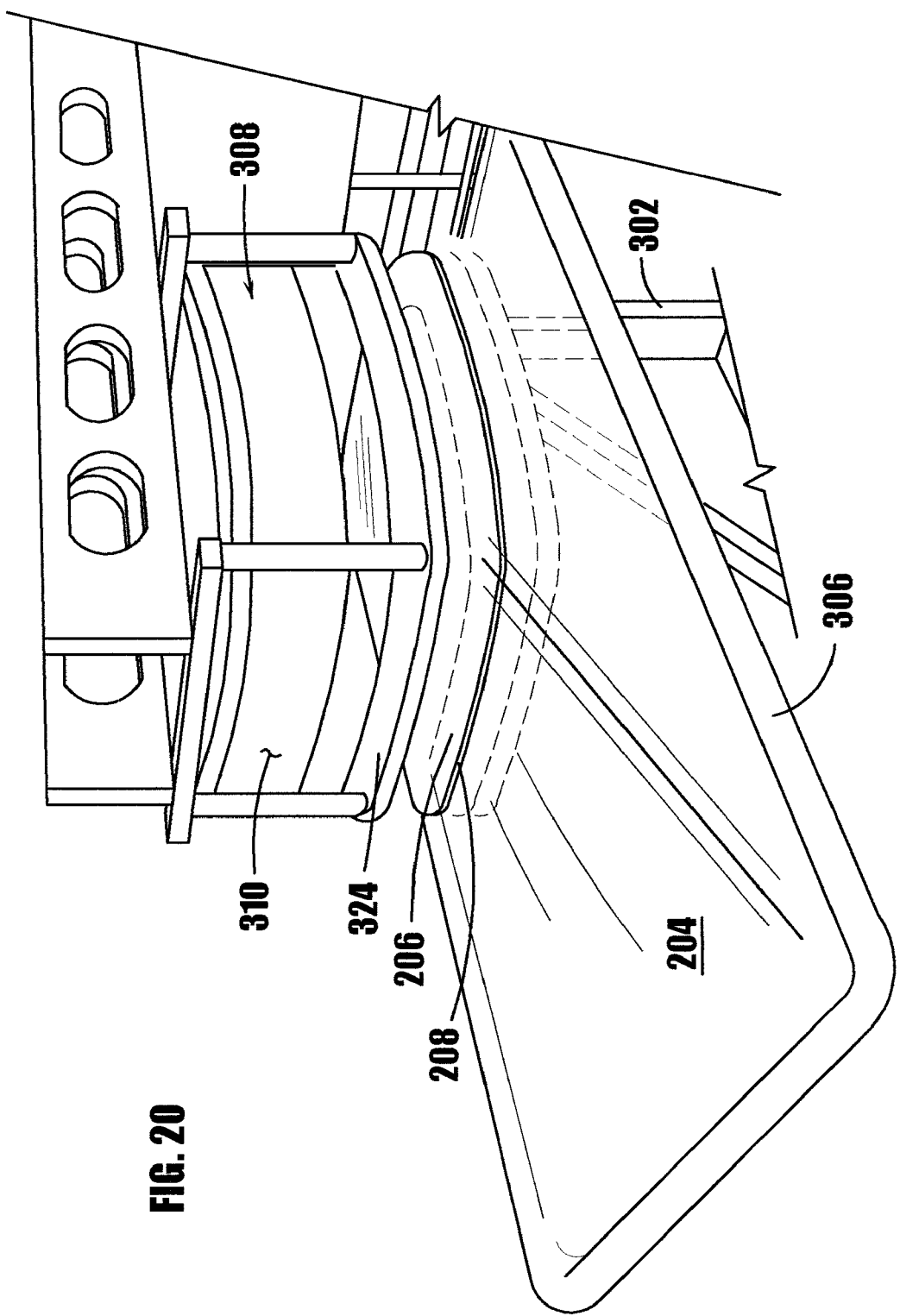
FIG. 20 is a partial, side perspective view of the apparatus of FIG. 12 with the tambourine mounted to the sterile bag.
Figure 21:
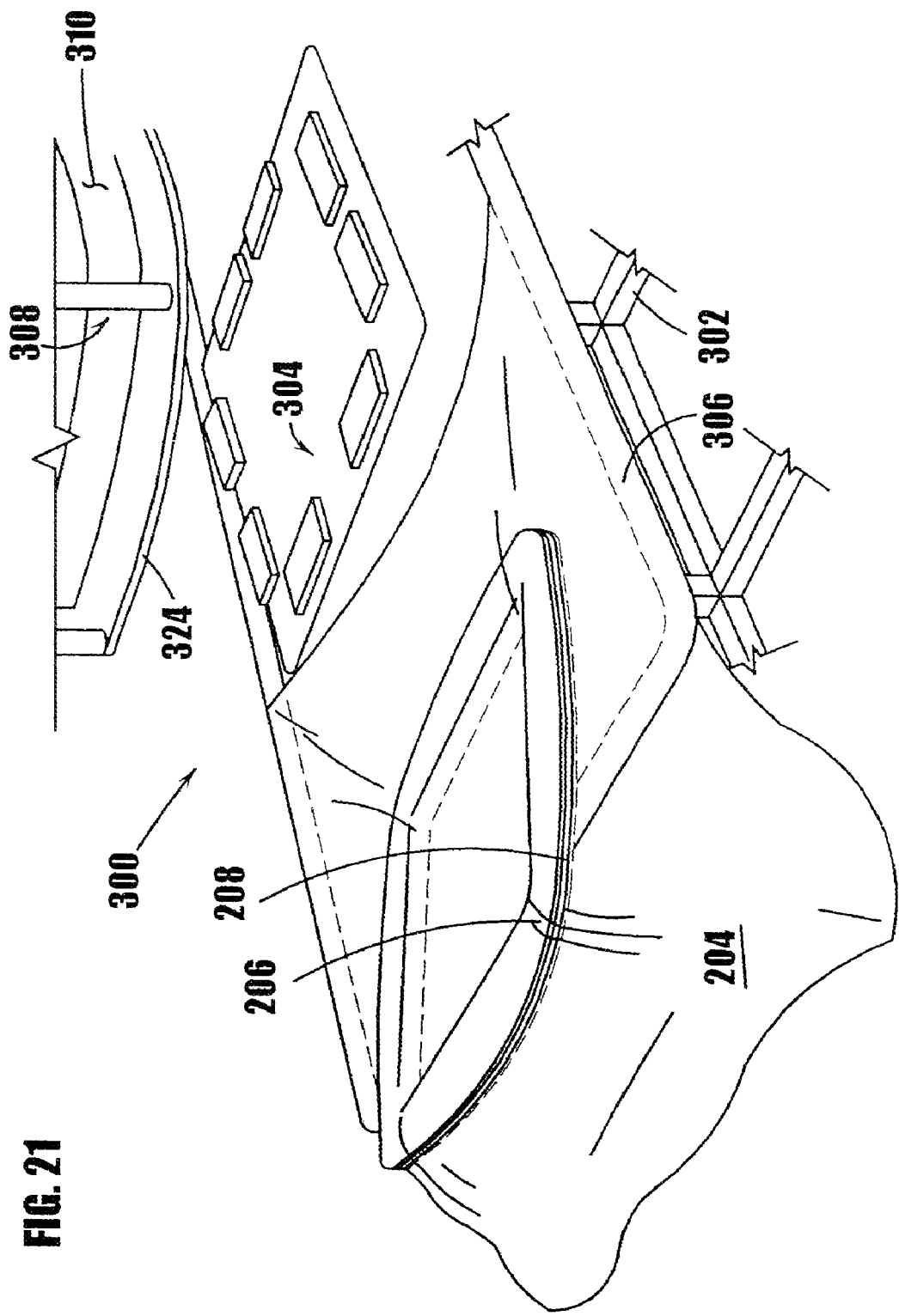
FIG. 21 illustrates an apparatus as shown in FIG. 12 with tambourine mounted to the sterile bag and the sterile bag partially removed from the apparatus.

Referring to FIGS. 17-21, a preferred process employing the apparatus 300 for attaching a tambourine 206 to a bag 204 is hereinafter described. Referring to FIG. 17, at least one elastic band 208 is installed on the first support surface 310 of the elastic fastener mount 308. Although not shown, it is also envisioned that a plurality of elastic bands 208 may be installed on the first surface 310 in an edge-to-edge relation extending vertically along the first support surface. A tambourine 206 is placed on the mount support 304, and as shown typically in FIG. 17, the open end of an intermediate bag 204 is slipped over the bag support 306 such that one wall of the bag overlies the tambourine and another wall of the bag underlies the tambourine. Preferably, the outer bag 204 is a polymeric bag that can withstand sterilization, such as by gamma or e-beam radiation. Then, the releasable backing 210 is placed against the second support surface 314 of the fastener mount assembly 308 and the vacuum source 318 is activated to hold the adhesive backed tape to the second support surface. The releasable backing of the tape facing the tambourine is removed either before mounting the tape to the second support surface 314, or after the tape is mounted to the second support surface to expose one side of the underlying adhesive to the portion of the bag overlying the tambourine. Referring to FIG. 18, the first lever 312 is activated downwardly to move the mount support 304 upwardly and, in turn, tension the portion of the bag 204 overlying the tambourine and thereby ready the bag for attachment of the elastic fastener and adhesive tape thereto. Then, as shown in FIG. 19, the second lever 313 is actuated to, in turn, move the fastener mount assembly 308 downwardly and into engagement with the tambourine. As shown in FIG. 19, the tensioning rim 324 of the fastener mount 308 further presses the portion of the bag extending about the periphery of the tambourine downwardly to facilitate attachment of the elastic fastener 208 to the tambourine. Also, upon contacting the tambourine, the exposed side of the adhesive 209 is pressed into engagement with the portion of the bag overlying the tambourine to, in turn, adhesively attach the tape to the bag. Then, as also shown in FIG. 19, the elastic fastener 208 is slipped downwardly off of the first support surface 310 of the fastener mount and into the peripheral groove of the tambourine. Upon attaching the adhesive and elastic fastener to the bag, and as shown in FIG. 20, the vacuum source is turned off to thereby release the tape from the second support surface 314, and the levers 312 and 313 are manipulated to move the mounts 304 and 308 away from each other. The bag, adhesive tape and tambourine assembly may then be slipped off of the bag support 304 and the apparatus 304 is ready to assemble another bag. The bag assembly may then be filled with the articles to be sterilized, and the open end of the bag may be heat sealed, or may be sealed in any of numerous different ways, in order to form an air-tight seal between the interior and exterior of the bag.

Figure 22:
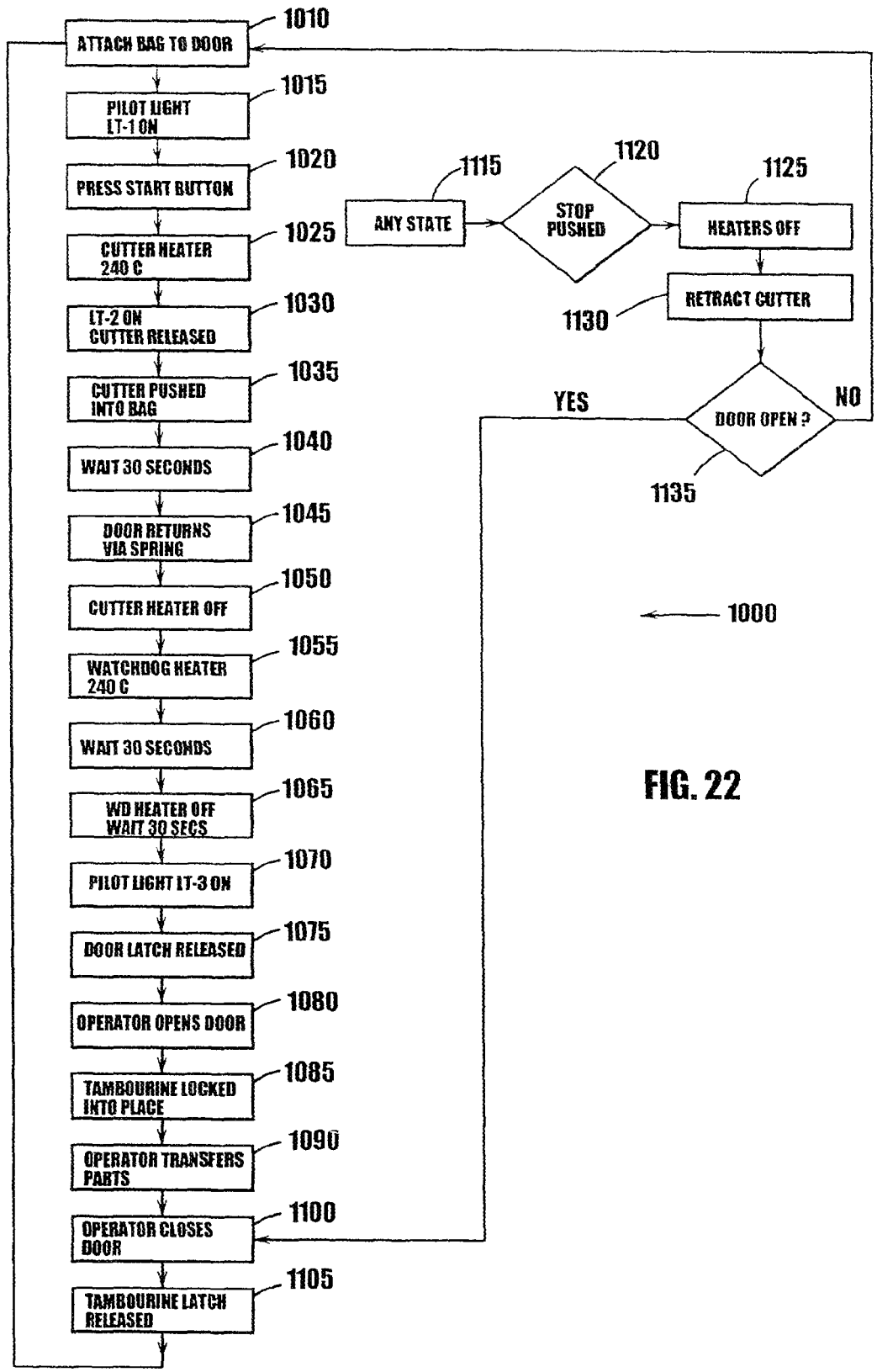
FIG. 22 is a process flow diagram detailing the various steps associated with transferring items from a sterile bag into an enclosure system constructed in accordance with a preferred embodiment of the subject disclosure.

Referring to FIG. 22, a preferred process 1000 for transferring sterile items from a sterile transfer bag system 200 into an enclosure 100 is illustrated. FIGS. 23-30 correspond generally with the process flow of FIG. 22. Preferably, the transfer bag system 200 is assembled as described above and loaded in a sterile environment. The transfer bag system 200 is then moved from the loading location to a desired location.

Figure 24:
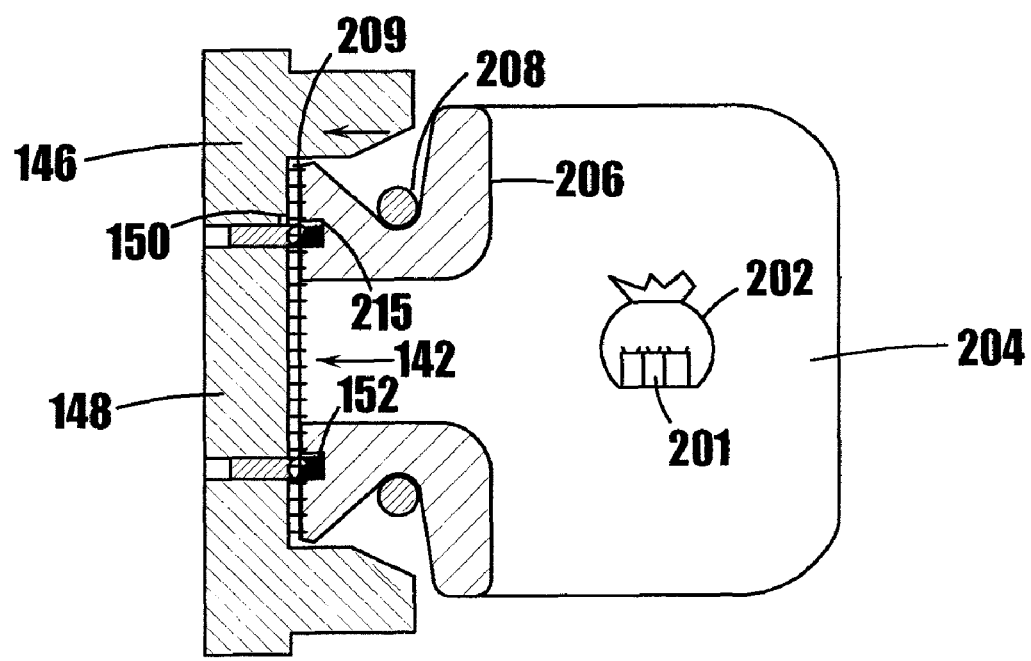
FIG. 24 illustrates a cross-sectional view of a transfer bag system mounted to the enclosure system of FIG. 1 prior to opening the transfer bag system.
Figure 25:
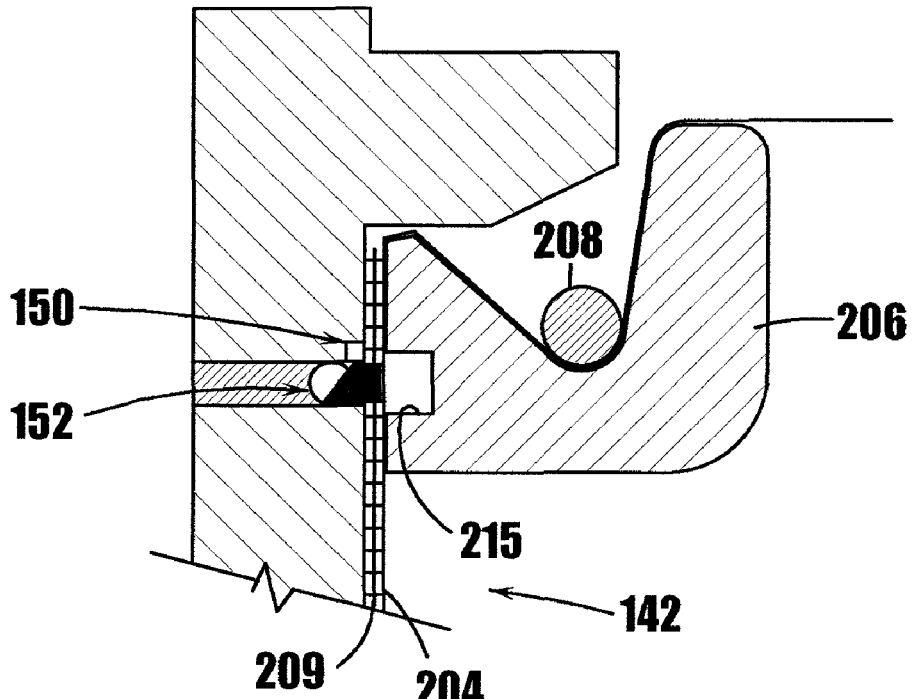
FIG. 25 illustrates a partial, cross-sectional view of a transfer bag system mounted to the enclosure system of FIG. 1 with the cutting heating element retracted.
Figure 26:
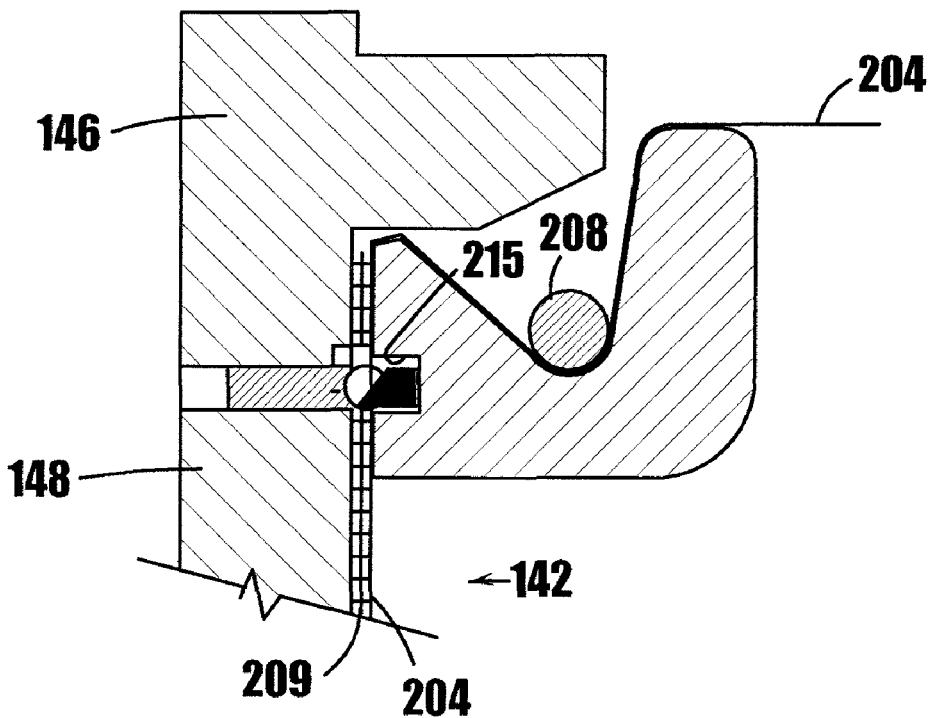
FIG. 26 illustrates a partial, cross-sectional view of a transfer bag system mounted to the enclosure system of FIG. 1 with the cutting heating element extended.

If necessary, the outer bag 212 (FIG. 9) is cleaned and removed in a staging area. At step 1010, the intermediate bag 204 is mounted to the enclosure 100 by removing the protective film 210, exposing the adhesive 209 and applying the rigid frame, mounting member or tambourine 206 about the window 142 (FIGS. 23 and 24). Preferably, the sterile items 201 contained in the inner bag 202 are placed upon the table and the enclosure 100 includes latching clamps 213 to releasably secure the frame 206 to the window 142. Preferably, the latching clamps 213 have sensors to electronically confirm complete closure of each latch and thereby ensure an air-tight seal between the transfer port and the tambourine. At step 1015, a button light 112 indicates power is on and the transfer port 140 is ready.

At step 1020, the operator presses the begin cycle button 114. At step 1025, the cutting element 152 heats up to temperature. At step 1030, upon the cutting element 152 reaching the required temperature, a light (not shown) in communication with the control system 160 indicates the cutting element 152 is at the desired temperature, preferably 240 degrees C. At step 1035 and as shown schematically in FIGS. 24-26, the drive mechanism 151 extends the cutting element 152 through the intermediate bag 204 into the groove 215 of the frame 206 to excise a portion thereof. After severing the intermediate bag 204, the cutting element 152 remains hot and extended. At step 1040, the heated and extended position of the cutting element 152 is maintained for a predetermined time period, preferably about 30 seconds. The excised portion of the bag 204 remains adhered to the port 148. In an alternative embodiment, the heated temperature and extended position of the cutting element 152 may be maintained in order to sterilize any contamination which may migrate from the excised portion.

At step 1045, the door 148 if open returns by default to a closed position to block the passage between the interior of the enclosure 100 and the interior of the intermediate bag 204. At step 1050, the cutting element 152 is deactivated and allowed to cool. At step 1055, the window heating element 150 is activated and heats up to a predetermined temperature preferably about 240 degree C. in order to sterilize the area about the periphery of the window 142. As can be seen, the heated cutting element 152 is slidably mounted in close proximity to, and is preferably substantially contiguous to, the window heating element 150. As a result, the heating element 150 and cutting element 152 cooperate to simultaneously excise the portion of the intermediate bag 204 and form the transfer passage therethrough, and to sterilize the peripheries of the window 142, intermediate bag 204 and the periphery of the excised portion of the intermediate bag 204 adhesively attached to the port 148.

Figure 27:
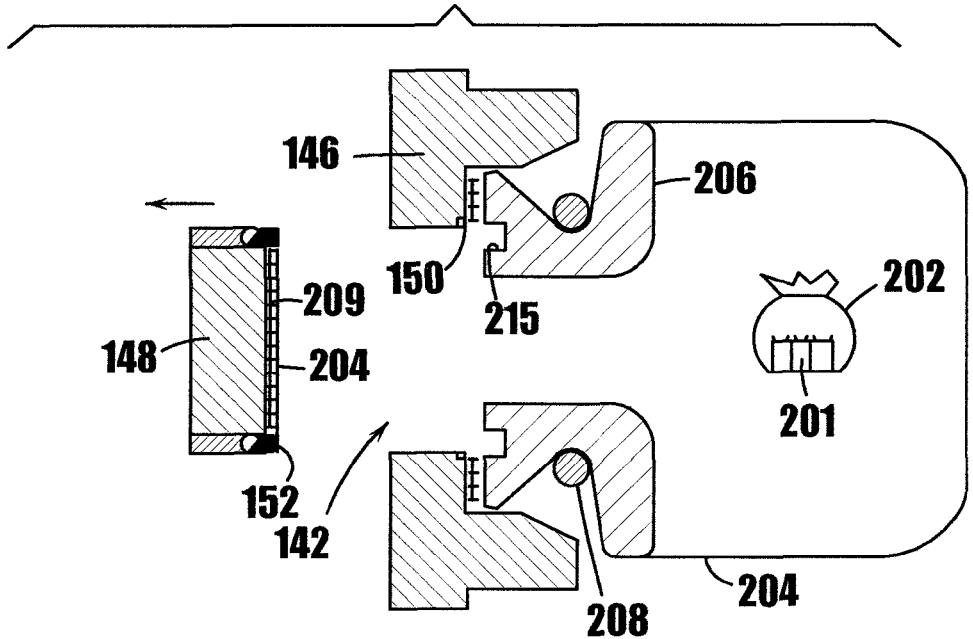
FIG. 27 illustrates a cross-sectional view of an open transfer bag system mounted to the enclosure system of FIG. 1.
Figure 28:
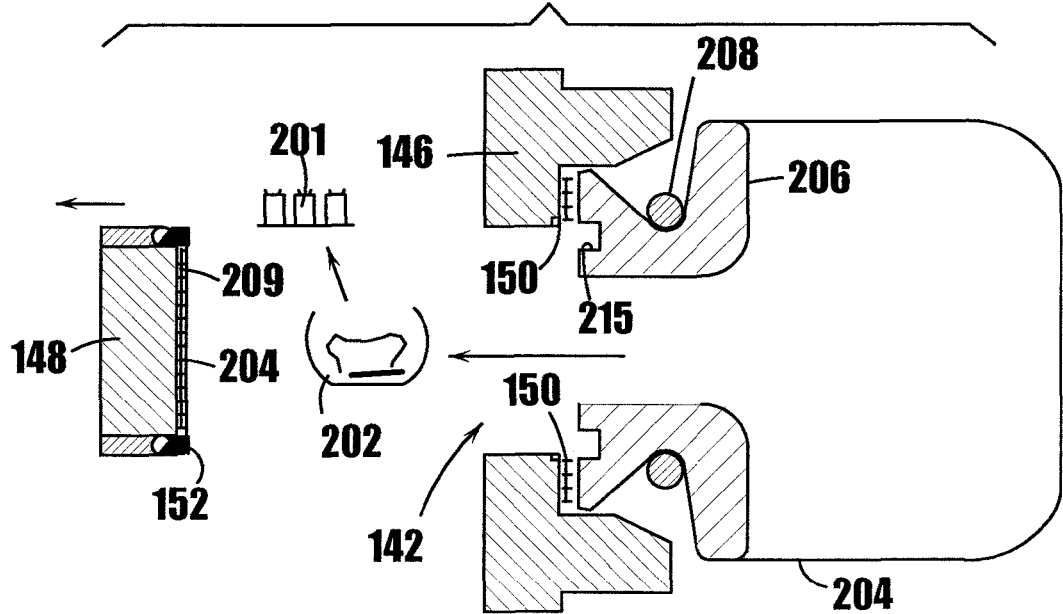
FIG. 28 illustrates a cross-sectional view of an open transfer bag system with the items transferred into the enclosure system of FIG. 1.

At step 1060, the control systems 160 waits a predetermined time period, e.g., about 30 seconds for the window heating element 150 to sterilize the area. At step 1065, the window heating element 150 is deactivated and a predetermined cool down period, e.g., about 30 seconds, is allowed to pass. In an alternative embodiment, the heated temperature of the window heating element 150 may be maintained to sterilize any contamination which may migrate from the intermediate bag 204 into the window 142 and, thereby the enclosure 100. As a result, the heated ring of concern defined by the heating element 150 of the window 142 is maintained contamination free. In other embodiments, one or both of the heating element 150 and the cutting element 152 are not continuously on but pulsed as would be known and appreciated by those of ordinary skill in the pertinent art. At step 1070, an indicator light (not shown) activates to indicate the transfer module 140 is ready for the next step. At step 1075, the handle 143 is manually released by the operator. At step 1080 and as shown in FIGS. 27 and 28, the operator depresses button 115 to open the door 148. At step 1085, the latches 213 continue to lock the frame 206 in place.

At step 1090, the inner bag 202 containing the sterilized items 201 is accessible by the operator. Preferably, the enclosure 100 has a sterile interface, such as articulated gloves, for allowing the operator to transfer the inner bag 202 from the transfer bag system 200 into the enclosure 100. Once the inner bag 202 is within the sterile enclosure 100, the items 201 are removed. Referring now to FIGS. 29 and 30, upon removal of the items 201 from the inner bag 202, the inner bag 202 becomes refuse. The operator can deposit the inner bag 202 and any other refuse into the intermediate bag 204 via the window 142. At step 1100, the operator activates the handle 143 to again close the port 148 to reseal the window 142. Upon closing of the port 148, the excised portion of the intermediate bag 204 is removed from the port 148 and discarded. At step 1105, the latches 213 are unlock the frame 206 from the transfer port 140 and the frame 206 is removed by the operator. Control passes back to step 1010 where the process can occur again.

In the event of an exigency, at step 1115, in any state the process 1000 can be halted in an orderly manner. At step 1120, the operator presses an emergency stop button (not shown) to terminate the process 1000 and control passes to step 1125. At step 1125, the control system 160 deactivates any heaters which may be activated. At step 1130, the heating cutting element 152 is retracted if not already retracted. At step 1135, the control system 160 queries a sensor (not shown) to determine if the port 148 is open. If the port 148 is not open, control passes to step 1010 where the process 1000 may be started again. If the port 148 is open, control passes to step 1100 where the port 148 is closed and the frame 206 is released as described above with respect to steps 1100 and 1105 such that the process 1000 can return to step 1010 where the process 1000 may begin again.

While the invention has been described with respect to preferred embodiments, those skilled in the art will readily appreciate that various changes and/or modifications can be made to the invention without departing from the spirit or scope of the invention. Accordingly, this detailed description of preferred embodiments is to be taken in an illustrative, as opposed to a limiting sense.

What is claimed is:

1. A method for sterile transfer of items sealed within a container, the method comprising the following steps:
   providing a transfer port having a door for sealing a transfer opening of the transfer port;
   providing a container having a mounting member thereon, an adhesive on an external surface of the container overlying the mounting member, and a releasable backing over said adhesive;
   removing the releasable backing; mounting a portion of the container to the transfer port with the adhesive so as to create a seal about the door;
   heating a heating element mounted about a peripheral portion of the door to a temperature sufficient to cut the container;
   moving the heating element on the door between retracted and extended positions to cut a portion of the container;
   heating a peripheral region of the transfer opening to prevent migration of contaminants therethrough;
   opening the door after cutting the container and heating the peripheral region of the transfer opening; and
   transferring at least one article from the container through the transfer opening.

2. A method as defined in claim 1, wherein the step of providing a container includes the steps of:
placing the at least one article in an inner container; and;
sealing the inner container within the container.

3. A method as defined in claim 2, further comprising the step of sterilizing via irradiation the second container and contents thereof.

4. A method as defined in claim 1, wherein the step of providing a container includes applying the adhesive to the external surface of the container and applying the releasable backing over said adhesive.

5. A method as defined in claim 2, further comprising the steps of:
sealing the container in an outer container;
transferring the outer container and contents thereof from one location to another; and
removing the outer container at the transfer port prior to the step of attaching the container to the transfer port.

6. A method as defined in claim 5, further comprising the step of sterilizing via irradiation the outer container and contents thereof.

7. A method as defined in claim 1, wherein the step of heating a peripheral region comprises heating an entire periphery of the transfer opening.

8. A method as defined in claim 1, wherein the step of heating a peripheral region comprises sterilizing the peripheral region.

9. A method as defined in claim 1, wherein the step of providing a transfer port comprises providing a sterile enclosure including the transfer port.

10. A method as defined in claim 9, wherein the transfer port is at least one of (i) mounted to a wall of the sterile enclosure, and (ii) formed by a wall of the sterile enclosure.

11. A method as defined in claim 9, further comprising transferring the at least one article into the sterile enclosure.

12. A method as defined in claim 11, further comprising closing the door and resealing the transfer opening.

13. A method as defined in claim 1, further comprising closing the door and resealing the transfer opening.

14. A method as defined in claim 13, further comprising maintaining the cut portion of the container against the door during at least one of (a) the step of cutting the portion of the container; (b) the step of opening the door; (c) the step of transferring the at least article from the container through the transfer opening; and (d) the step of closing the door.

15. A method as defined in claim 1, further comprising maintaining the cut portion of the container against the door during at least one of (a) the step of cutting the portion of the container; (b) the step of opening the door; and (c) the step of transferring the at least article from the container through the transfer opening.

16. A method as defined in claim 1, wherein the step of heating the heating element comprises heating the heating element to a temperature sufficient to sterilize the cut portion of the container and the step of moving the heating element further comprises sterilizing the portion of the container.

* * * * *